United States Patent [19]

Sciavolino

[11] 4,125,705

[45] Nov. 14, 1978

[54] SEMI-SYNTHETIC 4-AMINO-OLEANDOMYCIN DERIVATIVES

[75] Inventor: Frank C. Sciavolino, East Lyme, Conn.

[73] Assignee: Pfizer Inc., New York, N.Y.

[21] Appl. No.: 765,486

[22] Filed: Feb. 4, 1977

[51] Int. Cl.$^2$ .......................................... C07H 17/06
[52] U.S. Cl. .................................... 536/9; 424/180; 536/17
[58] Field of Search ............................... 536/9, 17

[56] References Cited

U.S. PATENT DOCUMENTS

| | | | |
|---|---|---|---|
| 3,022,219 | 2/1962 | Celmer | 536/17 |
| 3,179,652 | 4/1965 | Celmer | 536/17 |
| 3,842,069 | 10/1974 | Jones et al. | 536/9 |
| 4,036,853 | 7/1977 | Sciavolino | 260/295 AM |

Primary Examiner—Johnnie R. Brown
Attorney, Agent, or Firm—Francis X. Murphy; Charles J. Knuth; Albert E. Frost

[57] ABSTRACT

A series of 4"-deoxy-4"-amino-oleandomycin antibacterial agents and their preparation from semi-synthetic 4"-deoxy-4"-oxo-oleandomycin intermediates.

20 Claims, No Drawings

SEMI-SYNTHETIC 4″-AMINO-OLEANDOMYCIN DERIVATIVES

BACKGROUND OF THE INVENTION

Oleandomycin, its production in fermentation broths and its use as an antibacterial agent were first described in U.S. Pat. No. 2,757,123. The naturally occurring compound is known to have the following structure:

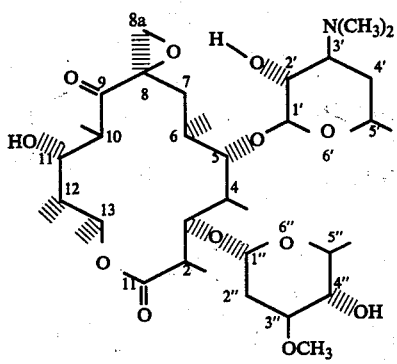

The conventionally accepted numbering scheme and stereochemical representation for oleandomycin and similar compounds is shown at a variety of positions.

Several synthetic modifications of this compound are known, particularly those in which from one to three of the free hydroxyl groups found at the 2′,4″ and 11-positions are esterified as acetyl esters. In addition, there are described in U.S. Pat. No. 3,022,219 similar modifications in which the acetyl in the above-mentioned esters is replaced with another, preferably unbranched lower alkanoyl of three to six carbon atoms.

SUMMARY OF THE INVENTION

The semi-synthetic oleandomycin antibacterial agents of this invention are represented by the formulae:

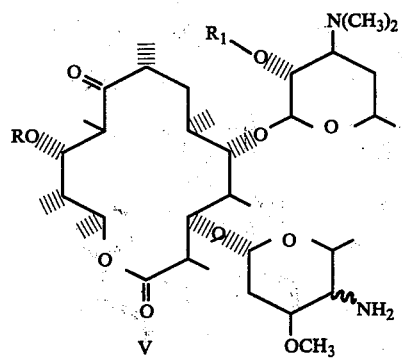

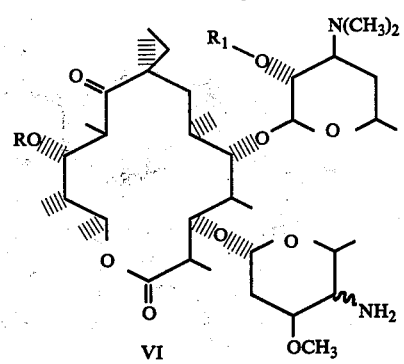

and the pharmaceutically acceptable acid addition salts thereof, wherein R and $R_1$ are each hydrogen or alkanoyl having two to three carbon atoms; $R_2$ is hydrogen or methyl; and $R_3$ is hydrogen or alkyl having from one to six carbon atoms provided that when $R_2$ is methyl, $R_3$ is methyl.

A preferred group of compounds within this class of chemotherapeutic agents are those of Formula IV. Especially preferred within this group are those compounds wherein $R_2$ and $R_3$ are each hydrogen and R is acetyl. Also preferred are compounds of Formulae V and VI wherein R is acetyl.

A second class of compounds of the present invention, useful as intermediates leading to the antibacterial compounds of Formulae IV, V and VI, are of the formulae:

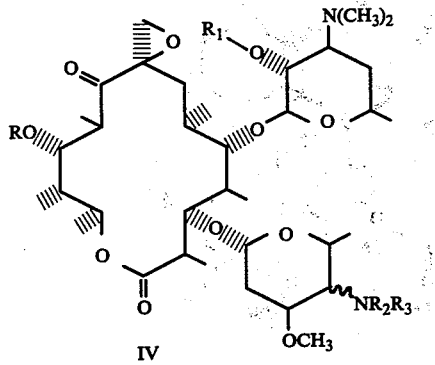

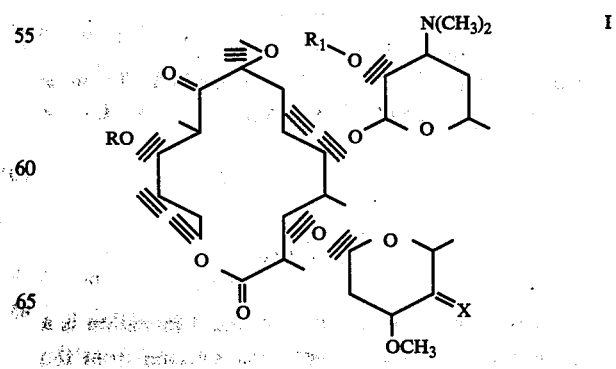

-continued

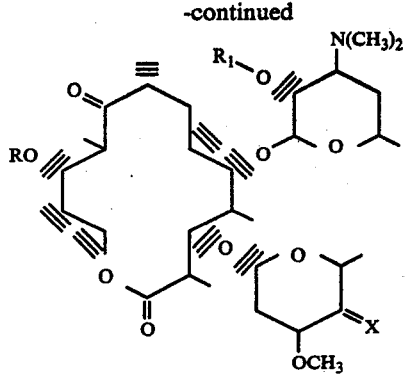
II

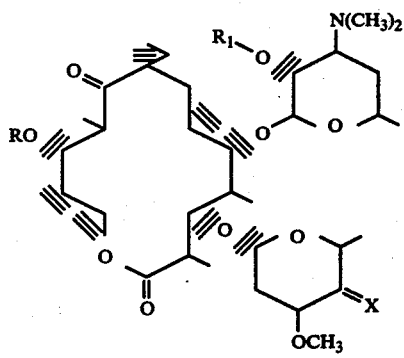
III wherein R and R₁ are each hydrogen or alkanoyl having from two to three carbon atoms; and X is O, N—OH, N—OCH₃ or

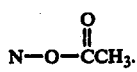

Preferred within this group of intermediates are those of Formula I wherein X is O, N—OH or

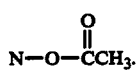

Also preferred are those intermediates of Formula II wherein X is O, N—OH or

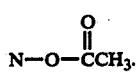

Finally, preferred within these intermediates are those compounds of Formula III wherein X is O, N—OH or

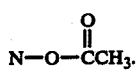

Also within the scope of the present invention is a process for preparing a compound selected from the formulae:

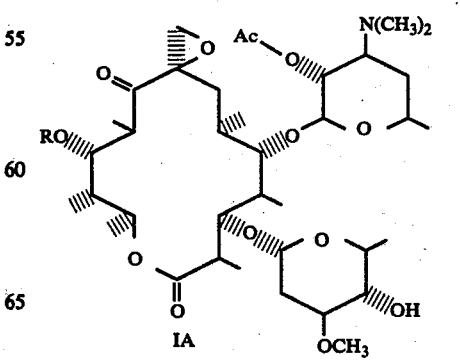

wherein Ac is alkanoyl having two to three carbon atoms and R is hydrogen or alkanoyl having two to three carbon atoms, which comprises reacting, respectively, a compound selected from those of the formulae:

-continued

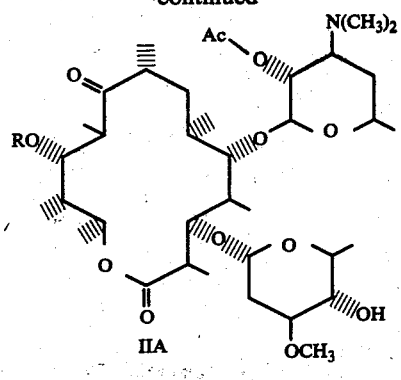
IIA

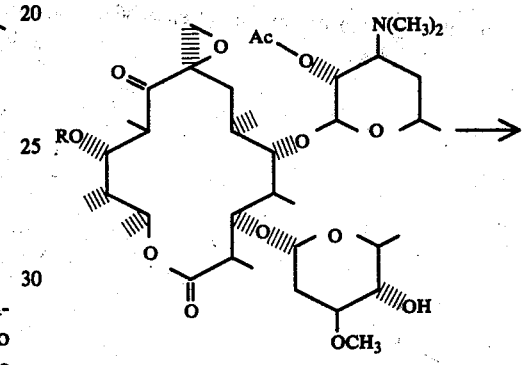
IA
(R = hydrogen or alkanoyl of
two to three carbon atoms; Ac =
alkanoyl of two to three carbon
atoms)

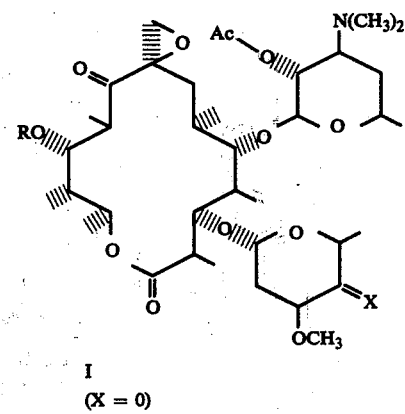
I
(X = O)

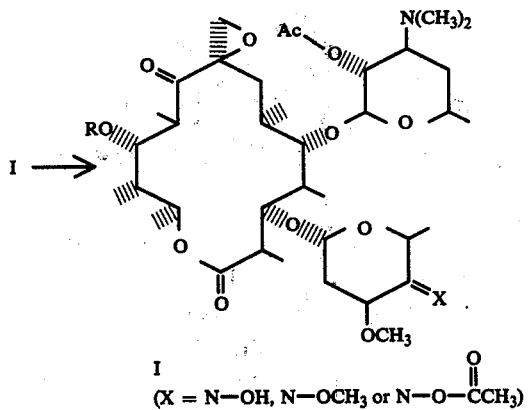
I
(X = N—OH, N—OCH$_3$ or N—O—$\overset{\overset{\text{O}}{\|}}{\text{C}}$CH$_3$)

IIIA with one mole each of N-chlorosuccinimide and dimethylsulfide in a reaction-inert-solvent at about 0° to −25° C. followed by contacting the reaction mixture with one mole of triethylamine.

A preferred feature of the claimed process is the oxidation of compounds of Formula IA wherein the solvent is toluene.

The compounds II, III, V and VI, although all derived from the natural occurring oleandomycin, differ in the structure at the 8-position. In the natural material, I and IV, this structure is an epoxide ring depicted as follows:

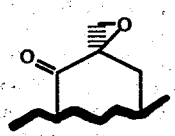

Compounds related to II and V contain a methyl group at the 8-position with the indicated sterochemistry and are depicted as follows:

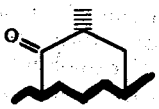

The nomenclature used to name the modified oleandomycins of Formulae II and V is 8,8a-deoxy-8,8a-dihydro-oleandomycin.

Those compounds of Formulae III and VI which contain a cyclopropyl ring at the 8-position are named as 8,8a-deoxy-8,8a-methylene-oleandomycin, and are depicted as follows:

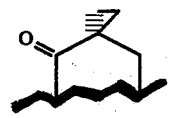

DETAILED DESCRIPTION OF THE INVENTION

In accordance with the process employed for synthesizing the 4"-deoxy-4"-amino-oleandomycin derived antibacterial agents of the present invention the following scheme, starting with a 11,2'-dialkanoyl- or 2'-alkanoyloleandomycin, is illustrative:

-continued

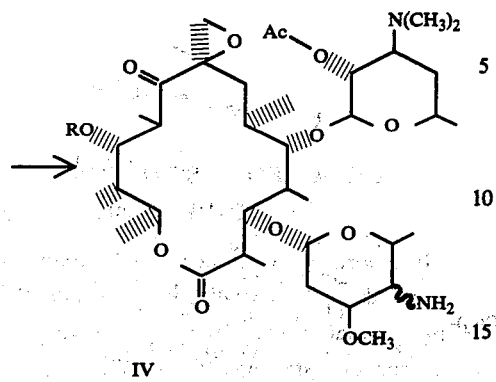

IV

The above described scheme is equally applicable to the conversion of compounds IIA and IIIA to the products V and VI, respectively, said compounds being of the formulae:

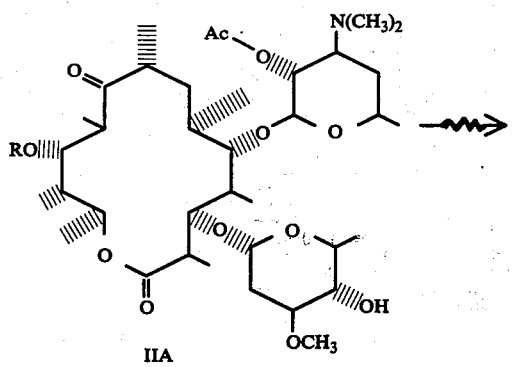

IIA and

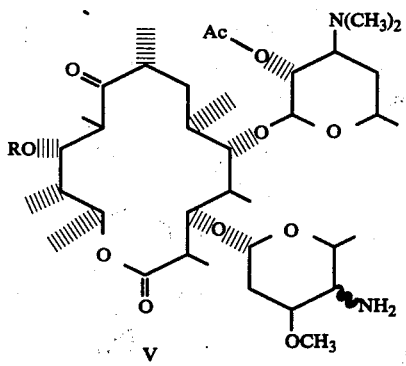

V

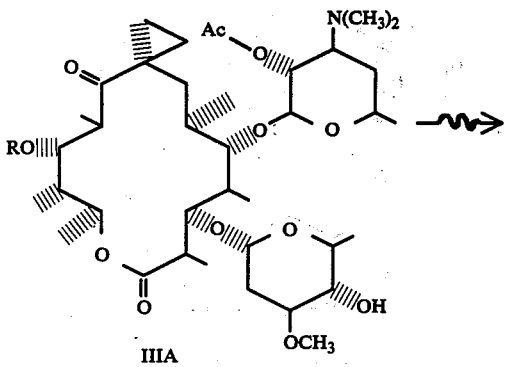

IIIA

-continued

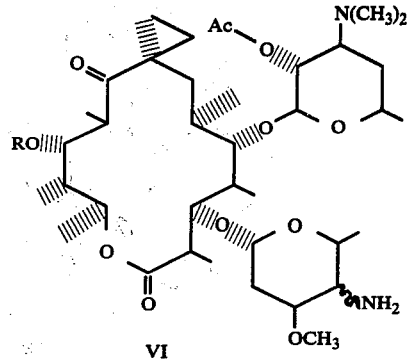

VI wherein R and Ac are as previously defined.

The initial reaction in these sequences is the selective oxidation of the 4"-hydroxy group and is the claimed process of the present invention. Said process comprises reacting the compounds IA, IIA or IIIA with N-chlorosuccinimide and dimethylsulfide, followed by the addition of a tertiary amine, such as triethylamine.

In practice, the N-chlorosuccinimide and dimethylsulfide are first combined together in a reaction-inert-solvent at about 0° C. After 10 to 20 minutes the temperature of the resulting mixture is adjusted to about 0° to −25° C., and substrate IA, IIA or IIIA is added while maintaining the aforementioned temperature. After 2 to 4 hours of reaction time the tertiary amine is added and the cooling bath removed.

Regarding the quantities of reactants, for each mole of alcohol substrate employed one mole each of N-chlorosuccinimide and dimethylsulfide are required. Experimentally, it is advantageous to employ a 1–20 fold excess of the succinimide and sulfide reactants in order to hasten the completion of the reaction. The tertiary amine employed should correspond to the molar amount of succinimide used.

The reaction-inert-solvent utilized in the claimed process should be one which appreciably solubilizes the reactants and does not react to any appreciable extent with either the reactants or the products formed. Since the reaction is conducted at about 0° to −25° C. it is preferred that, in addition to having the above characteristics, it should possess a freezing point below the reaction temperature. Such solvents or mixtures thereof which meet these criteria are toluene, ethyl acetate, chloroform, methylene chloride or tetrahydrofuran. Solvents which meet the above requirements but which have a freezing point above the reaction temperature can also be employed in minor amounts in combination with one or more of the preferred solvents. The especially preferred solvent for the claimed process is toluene containing benzene.

The claimed process is viewed as unique since the oxidation takes place at the 4"-position leaving the 11-position virtually uneffected when R is hydrogen.

Removal of the alkanoyl group at the 2'-position is carried out through a solvolysis reaction wherein the 2'-alkanoyl-4"-deoxy-4"-oxo-oleandomycin related compound is allowed to stir with an excess of methanol overnight at room temperature. Removal of the methanol and subsequent purification of the residual provides for compounds of Formula I, II or III wherein $R_1$ is hydrogen and X is O.

The hydroxy groups at positions 11 (R=H) and 2' ($R_1$=H) of the ketones (X=O) I, II or III can be acylated by treating said compounds with two moles of pyridine and an excess of the alkanoic anhydride at ice bath temperatures. In practice, the hydroxy containing compound is added to cooled alkanoic anhydride followed by the addition of the pyridine. When the additions are complete the ice bath is removed and the mixture allowed to stir overnight at room temperature. The product is obtained by hydrolysis of the reaction mixture with water and subsequent extraction of the product with ethyl acetate. Alternately, the excess alkanoic anhydride solvent can be removed under vacuum and the residual material purified by conventional means.

As previously indicated, the compounds I, II and III wherein X=O and R and $R_1$ are as previously defined are useful intermediates leading to the 4‴-amino antibacterial agents of the present invention. Preferred as intermediates within this group are 11,2′-diacetyl-4″-deoxy-4″-oxo-oleandomycin, 11-acetyl-4″-deoxy-4″-oxo-oleandomycin, 4″-deoxy-4″-oxo-oleandomycin, 2′-acetyl-4″-deoxy-4″-oxo-oleandomycin, 11,2′-diacetyl-8,8a-deoxy-8,8a-dihydro-4″-deoxy-4″-oxo-oleandomycin, 11-acetyl-8,8a-deoxy-8,8a-dihydro-4″-deoxy-4″-oxo-oleandomycin, 8,8a-deoxy-8,8a-dihydro-4″-deoxy-4″-oxo-oleandomycin, 2′-acetyl-8,8a-deoxy-8,8a-dihydro-4″-deoxy-4″-oxo-oleandomycin, 11,2′-diacetyl-8,8a-deoxy-8,8a-methylene-4″-deoxy-4″-oxo-oleandomycin, 11-acetyl-8,8a-deoxy-8,8a-methylene-4″-deoxy-4″-oxo-oleandomycin, 8,8a-deoxy-8,8a-methylene-4″-deoxy-4″-oxo-oleandomycin and 2′-acetyl-8,8a-deoxy-8,8a-methylene-4″-deoxy-4″-oxo-oleandomycin.

Several synethtic pathways can be employed in the preparation of the 4″-deoxy-4″-amino-oleandomycin derived compounds. The first comprises initial conversion of the 4″-deoxy-4″-oxo compounds to an oxime or oxime derivative, i.e., X = N—OH, N—OCH$_3$ or

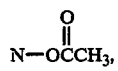
N—OCCH$_3$, followed by reduction of the oxime or derivative thereof to the amine of Formula IV ($R_2$, $R_3$ = H), V or VI.

The oximes of the ketones (X=O) are prepared by reacting said ketones with hydroxylamine hydrochloride in a solution of methanol-water at room temperature. In practice, it is preferred that an excess of hydroxylamine be employed, and as much as a three fold excess provides the desired intermediate in good yields. Employing ambient temperatures and an excess of the hydroxylamine allows for the preparation of the desired oxime derivative in a reaction period of 1 to 2 hours. The product is isolated by addition of the reaction mixture to water followed by basification to pH 9.5 and extraction with a water-immiscible solvent such as ethylacetate.

When O-methylhydroxylamine hydrochloride is employed in place of hydroxylamine hydrochloride, the reaction provides the O-methyloxime derivative. When using O-methylhydroxylamine, it is preferred to extend the reaction time to 6 to 12 hours. Isolation of the product is carried out in the same manner as previously described for the oxime derivative.

Preparation of the O-acetyloxime compounds

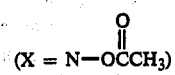
(X = N—OCCH$_3$)

is effected by acetylation of the corresponding oxime. Experimentally, one mole of the oxime is reacted with one mole of acetic anhydride in the presence of one mole of pyridine. The use of an excess of the anhydride and pyridine aid in the completion of the reaction and an excess of two to three fold is preferred. The reaction is best conducted in an aprotic hydrocarbon solvent such as benzene or toluene at room temperature overnight. On completion of the reaction, water is added and the product is separated in the hydrocarbon layer. Alternatively, O-acetyl derivatives can be prepared by treating the requisite ketone with O-acetylhydroxylamine hydrochloride under reaction conditions operable in the preparation of the oxime derivatives.

The preferred oxime and oxime derivatives which are useful intermediates leading to the 4″-deoxy-4″-amino-oleandomycin derived antibacterial agents include 11,2′-diacetyl-4″-deoxy-4″-oxo-oleandomycin oxime, 11-acetyl-4″-deoxy-4″-oxo-oleandomycin oxime, 11,2′-diacetyl-4″-deoxy-4″-oxo-oleandomycin O-acetyloxime, 11-acetyl-4″-deoxy-4″-oxo-oleandomycin O-acetyloxime, 11,2′-diacetyl-8,8a-deoxy-8,8a-dihydro-4″-deoxy-4″-oxo-oleandomycin oxime, 11-acetyl-8,8a-deoxy-8,8a-dihydro-4″-deoxy-4″-oxo-oleandomycin oxime, 11,2′-diacetyl-8,8a-deoxy-8,8a-dihydro-4″-deoxy-4″-oxo-oleandomycin O-acetyloxime, 11-acetyl-8,8a-deoxy-8,8a-dihydro-4″-deoxy-4″-oxo-oleandomycin O-acetyloxime, 11,2′-diacetyl-8,8a-deoxy-8,8a-methylene-4″-deoxy-4″-oxo-oleandomycin oxime, 11-acetyl-8,8a-deoxy-8,8a-methylene-4″-deoxy-4″-oxo-oleandomycin oxime, 11,2′-diacetyl-8,8a-deoxy-8,8a-methylene-4″-deoxy-4″-oxo-oleandomycin O-acetyloxime and 11-acetyl-8,8a-deoxy-8,8a-methylene-4″-deoxy-4″-oxo-oleandomycin O-acetyloxime.

Reduction of the ketone derivatives (X=N—OH, N—OCH$_3$ or

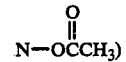
N—OCCH$_3$)

is carried out by a catalytic hydrogenation wherein a solution of the oxime or derivative thereof in a lower alkanol, such as isopropanol, and a Raney nickel, 10%-palladium-on-charcoal or platinum oxide catalyst is shaken in a hydrogen atmosphere at an initial pressure of 50 p.s.i. at room temperature overnight. Filtration of the spent catalyst followed by removal of the solvent from the filtrate provides for the isolation of the desired 4″-deoxy-4″-amino substituted antibacterial agent of the Formulae IV, V or VI. If methanol is employed as the reduction solvent, solvolysis of the 2′-alkanoyl group will occur. To avoid removal of this moiety, isopropanol is the preferred solvent.

The second, and preferred, route from the ketones (X=O) of Formulae I, II and III to the primary amines of Formulae IV, V and VI comprises the condensation of said ketones with the ammonium salt of a lower alkanoic acid and the subsequent reduction of the in situ generated imine. In addition to ammonium salts of lower alkanoic acid being operable, other ammonium salts such as those of inorganic acids can also be employed.

In practice, a solution of the ketone I, II or III (X=O) in a lower alkanol such as methanol is treated with an ammonium salt of an alkanoic acid such as acetic acid and the cooled reaction mixture treated with the reducing agent sodium cyanoborohydride. The reaction is allowed to proceed at room temperature for several hours, and is subsequently hydrolyzed and the product isolated.

Although one mole of ammonium alkanoate is needed per mole of ketone, it is advantageous to add an excess in order to ensure a rapid formation of the imine. As large as a 10 fold excess can be employed without effecting the quality of the final product.

Regarding the amount of the reducing agent to be employed per mole of ketone, it is preferred that about two moles of sodium cyanoborohydride per mole of ketone be used.

The reaction time for the reduction varies from 2 to 3 hours at ambient temperatures.

As previously mentioned, the preferred solvent is methanol while the preferred ammonium alkanoate is ammonium acetate. Isopropanol can also be used as a solvent, and is especially desirable when solvolysis of the 2'-alkanoyl group is to be avoided.

In isolating the desired 4"-deoxy-4"-amino-oleandomycin derivatives from any non-basic by-products or starting material, advantage is taken of the basic nature of the final product. Accordingly, an aqueous solution of the product is extracted over a range of gradual increasing pH such that neutral or non-basic materials are extracted at lower pH's and the product at a pH of about 9. The extracting solvents, either ethyl acetate or diethyl ether, are backwashed with brine and water, dried over sodium sulfate and obtained by removal of the solvent.

Additional purification, if necessary, can be effected by column chromatography on silica gel according to known procedures.

The aforementioned reductive amination can be carried out with other reducing conditions besides the use of sodium cyanoborohydride. Certain noble metal catalysts, such as palladium-on-charcoal, can be employed with hydrogen and an ammonium alkanoate to effectively provide for the conversion of compounds of Formulae I, II and III (X=O) to those of Formulae IV, V and VI, respectively.

Experimentally, a solution of the appropriate ketone in a lower alkanol, such as methanol or isopropanol, is treated with an ammonium alkanoate, such as ammonium acetate, and 10% palladium-on-charcoal, and the resulting suspension shaken in a hydrogen atmosphere at temperatures of about 25°–50° C. until the theoretical amount of hydrogen has been absorbed.

Regarding the ratio of reactants, it is preferred that a 10 fold excess of the ammonium alkanoate be employed to ensure complete reaction in a reasonable time period. The amount of the catalyst can vary from 10% to 50%, on a weight basis, of the starting ketone. The initial pressure of the hydrogen is not critical, and a pressure from one atmosphere to 500 p.s.i. is preferred to shorten the reaction time. Employing the aforementioned parameters, the reaction time will vary between 2 to 6 hours.

At the conclusion of the reductive amination reaction, the spent catalyst is filtered and the filtrate concentrated to dryness. Purification of the product is carried out by the aforementioned procedure wherein sodium cyanoborohydride is used as the reducing agent.

Synthesis of antibacterial compounds of Formula IV wherein $R_2$ is hydrogen and $R_3$ is alkyl of one to six carbon atoms is conveniently achieved from the ketone I (X=O) and the appropriate amine, $R_3NH_2$, using sodium cyanoborohydride as the reducing agent. In order to maintain the pH between about 6 and 7, a molar amount of an alkanoic acid, such as acetic acid, equal to that of the amine is employed. Alternately, a corresponding amount of hydrogen chloride gas can also be employed in place of the alkanoic acid.

The ratio of reactants, reaction temperature and time and work-up of the reductive amination reaction are the same as the corresponding parameters for the reaction leading to those compounds wherein $R_2$ and $R_3$ are each hydrogen and sodium cyanoborohydride is employed as the reducing agent.

The antibacterial compounds IV wherein $R_2$ and $R_3$ are each methyl are prepared by the reductive alkylation of the 4"-deoxy-4"-amino-oleandomycin IV wherein $R_2$ and $R_3$ are each hydrogen using formaldehyde, hydrogen and 10% palladium-on-charcoal.

The ratio of reactants, reaction temperature, solvent, pressure, time and work-up are the same as those parameters for the reaction leading to IV wherein $R_2$ and $R_3$ are each hydrogen and hydrogen gas and 10% palladium are employed as the reducing agent.

As previously mentioned, solvolysis of the 2'-alkanoyl moiety can be effected by allowing said derivative of the amine related to IV, V or VI to stir in a methanol solution overnight at ambient temperatures.

Preferred among these compounds because of their antibacterial utility are 4"'-deoxy-4"-amino-oleandomycin, 11-acetyl-4"-deoxy-4"-amino-oleandomycin, 11,2'-diacetyl-4"-deoxy-4"-amino-oleandomycin, 11-acetyl-8,8a-deoxy-8,8a-dihydro-4"-deoxy-4"-amino-oleandomycin, 11,2'-diacetyl-8,8a-deoxy-8,8a-dihydro-4"-deoxy-4"-amino-oleandomycin, 11-acetyl-8,8a-deoxy-8,8a-methylene-4"-deoxy-4"-amino-oleandomycin and 11,2'-diacetyl-8,8a-deoxy-8,8a-methylene-4"-deoxy-4"-amino-oleandomycin.

In the utilization of the chemotherapeutic activity of those compounds of the present invention which form salts, it is preferred, of course, to use pharmaceutically acceptable salts. Although water-insolubility, high toxicity, or lack of crystalline nature may make some particular salt species unsuitable or less desirable for use as such in a given pharmaceutical application, the water insoluble or toxic salts can be converted to the corresponding pharmaceutically acceptable bases by decomposition of the salt as described above, or alternately they can be converted to any desired pharmaceutically acceptable acid addition salt.

Examples of acids which provide pharmaceutically acceptable anions are hydrochloric, hydrobromic, hydroiodic, nitric, sulfuric, or sulfurous, phosphoric, acetic, lactic, citric, tartaric, succinic, maleic, gluconic and aspartic acids.

The stereochemistry of the starting materials leading to the antibacterial agents of the present invention is that of the natural material. The oxidation of the 4"-hydroxyl group to a ketone and the subsequent conversion of said ketone to the 4"-amines presents an opportunity for the stereochemistry of the 4"-substituent to change from that of the natural product. Accordingly, when the compounds I, II and III (X=O) are converted to amines by one of the hereinbefore described procedures, it is possible that two epimeric amines are formed. Experimentally, it is observed that both epimeric amines are present in the final product in varying ratios depending on the choice of synthetic method. If the isolated product consists predominantly of one of the epimers, said epimer can be purified by repeated recrystallization from a suitable solvent to a constant melting point. The other epimer, the one present in smaller amounts in the originally isolated solid material, is the predominant product in the mother liquor. It can be recovered therefrom by methods known to those skilled in the art, as for example, the evaporation of the mother liquor and repeated recrystallization of the residue to a product of constant melting point or by chromatography.

Although said mixture of epimers can be separated by methods known to those skilled in the art, for practical reasons it is advantageous to use said mixture as it is isolated from the reaction. However, it is frequently advantageous to purify the mixture of epimers by at least one recrystallization from an appropriate solvent, subjecting it to column chromatography, solvent partitioning or by trituration in an appropriate solvent. Said purification, while not necessarily separating the epimers, removes such extraneous materials as starting materials and undesirable by-products.

The absolute stereochemical assignment for the epimers has not been completed. Both epimers of a given compound, however, exhibit the same type of activity, e.g., as antibacterial agents.

The novel 4''-deoxy-4''-amino-oleandomycin derivatives described herein exhibit in vitro activity against a variety of Gram-positive microorganisms such as *Staphylococcus aureus* and *Streptococcus pyogenes* and against certain Gram-negative microorganisms such as those of spherical or ellipsoidal shape (cocci). Their activity is readily demonstrated by in vitro tests against various microorganisms in a brain-heart infusion medium by the usual two-fold serial dilution technique. Their in vitro activity renders them useful for topical application in the form of ointments, creams and the like; for sterilization purposes, e.g., sick-room utensils; and as industrial antimicrobials, for example, in water treatment, slime control, paint and wood preservation.

For in vitro use, e.g., for topical application, it will often be convenient to compound the selected product with a pharmaceutically-acceptable carrier such as vegetable or mineral oil or an emollient cream. Similarly, they may be dissolved or dispersed in liquid carriers or solvents, such as water, alcohol, glycols or mixtures thereof or other pharmaceutically-acceptable inert media; that is, media which have no harmful effect on the active ingredient. For such purposes, it will generally be acceptable to employ concentrations of active ingredients of from about 0.01 percent to about 10 percent by weight based on total composition.

Additionally, many compounds of this invention are active versus Gram-positive and certain Gram-negative microorganisms in vivo such as *Pasteurella multocida* and *Neisseria sicca* via the oral and/or parenteral routes of administration in animals, including man. Their in vivo activity is more limited as regards susceptible organisms and is determined by the usual procedure which comprises mice of substantially uniform weight with the test organism and subsequently treating them orally or subcutaneously with the test compound. In practice, the mice, e.g. 10, are given an intraperitoneal inoculation of suitably diluted cultures containing approximately 1 to 10 times the $LD_{100}$ (the lowest concentration of organisms required to produce 100% deaths). Control tests are simultaneously run in which mice receive inoculum of lower dilutions as a check on possible variation in virulence of the test organism. The test compound is administered 0.5 hour post-inoculation, and is repeated 4, 24 and 48 hours later. Surviving mice are held for 4 days after the last treatment and the number of survivors is noted.

When used in vivo, these novel compounds can be administered orally or parenterally, e.g., by subcutaneous or intramuscular injection, at a dosage of from about 1 mg./kg. to about 200 mg./kg. of body weight per day. The favored dosage range is from about 5 mg./kg. to about 100 mg./kg. of body weight per day and the preferred range from about 5 mg./kg. to about 50 mg./kg. of body weight per day. Vehicles suitable for parenteral injection may be either aqueous such as water, isotonic saline, isotonic dextrose, Ringers' solution, or non-aqueous such as fatty oils of vegetable origin (cotton seed, peanut oil, corn, sesame), dimethylsulfoxide and other non-aqueous vehicles which will not interfere with therapeutic efficiency of the preparation and are non-toxic in the volume or proportion used (glycerol, propylene glycol, sorbitol). Additionally, compositions suitable for extemporaneous preparation of solutions prior to administration may advantageously be made. Such compositions may include liquid diluents, for example, propylene glycol, diethyl carbonate, glycerol, sorbitol, etc.; buffering agents, hyaluronidase, local anesthetics and inorganic salts to afford desirable pharmacological properties. These compounds may also be combined with various pharmaceutically-acceptable inert carriers including solid diluents, aqueous vehicles, non-toxic organic solvents in the form of capsules, tablets, lozenges, troches, dry mixes, suspensions, solutions, elixirs and parenteral solutions or suspensions. In general, the compounds are used in various dosage forms at concentration levels ranging from about 0.5 percent to about 90 percent by weight of the total composition.

The following examples are provided solely for the purpose of illustration and are not to be construed as limitations of this invention, many variations of which are possible without departing from the spirit or scope thereof.

EXAMPLE 1

2'-Acetyl-4''-deoxy-4''-oxo-oleandomycin

Dimethylsulfide (0.337 ml.) is added to a turbid solution of 467 mg. of N-chlorosuccinimide in 20 ml. of toluene and 6 ml. of benzene cooled to −5° C. and maintained under a nitrogen atmosphere. After stirring at 0° C. for 20 min. the mixture is cooled to −25° C. and 1.46 g. of 2'-acetyloleandomycin and 15 ml. of toluene are added. Stirring is continued for 2 hrs. at −20° C. followed by the addition of 0.46 ml. of triethylamine. The reaction mixture is maintained at −20° C. for an additional 5 min. and then allowed to warm to 0° C. The mixture is poured, with stirring, into 50 ml. of water and 50 ml. of ethyl acetate. The pH of the aqueous mixture is adjusted to 9.5 by the addition of aqueous sodium hydroxide solution. The organic layer is subsequently separated, dried over sodium sulfate and concentrated in vacuo to a white foam (1.5 g.). Trituration with diethyl ether gives 864 mg. of crude product, which on recrystallization twice from methylene chloride-diethyl ether gives 212 mg. of the pure product, m.p. 183°–185.5° C.

Anal. Calc'd for $C_{37}H_{61}O_{13}N$: C, 61.1; H, 8.5; N, 1.9. Found: C, 60.9; H, 8.4; N, 1.9.

NMR ($\delta$, $CDCl_3$): 5.60 (1H)m, 3.50 (3H)s, 2.73 (2H)m, 2.23 (6H)s and 2.03 (3H)s.

Employing the above procedure and starting with 2'-propionyloleandomycin, there is obtained 2'-propionyl-4"-deoxy-4"-oxo-oleandomycin.

EXAMPLE 2

4"-Deoxy-4"-oxo-oleandomycin

A solution of 1.0 g. of 2'-acetyl-4"-deoxy-4"-oxo-oleandomycin in 20 ml. of methanol is allowed to stir at room temperature overnight. The solution is concentrated in vacuo to give the desired product as a white foam, 937 mg.

NMR ($\delta$, $CDCl_3$): 5.60 (1H)m, 3.50 (3H)s, 2.85 (2H)m and 2.26 (6H)s.

EXAMPLE 3

11,2'-Diacetyl-4"-deoxy-4"-oxo-oleandomycin

A. Via Acetylation

To 4.0 ml. of acetic anhydride under a nitrogen atmosphere and cooled to 0° C. in an ice bath is added 727 mg. of 2'-acetyl-4"-deoxy-4"-oxo-oleandomycin. After 5 min., 0.158 ml. of pyridine is added and the hazy suspension allowed to stir overnight at room temperature. The resulting solution is quenched in water layered over with ethyl acetate, and the pH adjusted to 7.2 by the addition of solid sodium bicarbonate and then to 9.5 using a 1N sodium hydroxide solution. The organic layer is separated, washed successively with water and a saturated brine solution and dried over sodium sulfate. Removal of the solution under reduced pressure gives 588 mg. of the desired product.

NMR ($\delta$, $CDCl_3$): 3.48 (3H)s, 2.63 (2H)m, 2.26 (6H)s and 2.06 (6H)s.

Repeating this procedure and employing the requisite 2'-alkanoyl-4"-deoxy-4"-oxo-oleandomycin and acylating reagent, the following compounds are synthesized: 11-acetyl-2'-propionyl-4"-deoxy-4"-oxo-oleandomycin, 11-propionyl-2'-acetyl-4"-deoxy-4"-oxo-oleandomycin and 11,2'-dipropionyl-4"-deoxy-4"-oxo-oleandomycin.

B. Via Oxidation

To 4.5 g. of N-chlorosuccinimide, 50 ml. of benzene and 150 ml. of toluene in a dry flask fitted with a magnetic stirrer and nitrogen inlet and cooled to −5° C. is added 3.36 ml. of dimethylsulfide. After stirring at 0° C. for 20 min., the contents are cooled to −25° C. and treated with 5.0 g. of 11,2'-diacetyl-oleandomycin in 100 ml. of toluene. Cooling and stirring are continued for 2 hrs. followed by the addition of 4.73 ml. of triethylamine. The reaction mixture is allowed to stir at 0° C. for 15 min., and is subsequently poured into 500 ml. of water. The pH is adjusted to 9.5 with 1N aqueous sodium hydroxide and the organic layer separated, washed with water and a brine solution and dried over sodium sulfate. Removal of the solvent in vacuo gives 4.9 g. of the desired product, identical to that prepared in Example 3A, as a foam.

NMR ($\delta$, $CDCl_3$): 3.48 (3H)s, 2.61 (2H)m, 2.23 (6H)s and 2.03 (6H)s.

EXAMPLE 4

11-Acetyl-4"-deoxy-4"-oxo-oleandomycin

A solution of 4.0 g. of 11,2'-diacetyl-4"-deoxy-4"-oxo-oleandomycin in 75 ml. of methanol is allowed to stir at room temperature overnight. The reaction mixture is concentrated under reduced pressure to give the product as a foam. A diethyl ether solution of the residue, on treatment with hexane, gives 2.6 g. of the product as a white solid, m.p. 112°–117° C.

NMR ($\delta$, $CDCl_3$): 3.43 (3H)s, 2.60 (2H)m, 2.23 (6H)s and 2.01 (3H)s.

Similarly, by employing 11,2'-dipropionyl-4"-deoxy-4"-oxo-oleandomycin or 11-propionyl-2'-acetyl-4"-deoxy-4"-oxo-oleandomycin in the above procedure, 11-propionyl-4"-deoxy-4"-oxo-oleandomycin is prepared.

EXAMPLE 5

11,2'-Diacetyl-4"-deoxy-4"-oxo-oleandomycin

A reaction mixture comprising 1.0 g. of 11,2'-diacetyl-oleandomycin, 7.09 ml. of dimethylsulfoxide and 9.44 ml. of acetic anhydride is allowed to stir at room temperature for 4 days. The resulting yellow solution is added to water layered over with benzene. The pH is subsequently adjusted with aqueous 1N sodium hydroxide to 9.5 and the organic layer separated, dried over sodium sulfate and concentrated in vacuo to dryness. The yellow oily foam (1.14 g.) is chromatographed over 20 g. of silica gel using chloroform-acetone/9:1 as the eluate. Removal of the solvent from the fractions gives 800 mg. of the desired product and 110 mg. of a by-product.

In a similar manner, when 11-acetyl-2'-propionyloleandomycin, 11,2'-dipropionyloleandomycin or 11-propionyl-2'-acetyloleandomycin is employed as the starting material in the above oxidation procedure, 11-acetyl-2'-propionyl-4"-deoxy-4"-oxo-oleandomycin, 11,2'-dipropionyl-4"-deoxy-4"-oxo-oleandomycin and 11-propionyl-2'-acetyl-4"-deoxy-4"-oxo-oleandomycin are obtained, respectively.

EXAMPLE 6

2'-Acetyl-8,8a-deoxy-8,8a-dihydro-4"-deoxy-4"-oxo-oleandomycin

To a dry flask fitted with a magnetic stirrer and nitrogen inlet containing 11.6 g. of N-chlorosuccinimide, 750 ml. of toluene and 250 ml. of benzene and cooled to −5° C. is added 6.0 ml. of dimethylsulfide, and the resulting solution allowed to stir for 20 min. The temperature is further lowered to −20° C. and 25 g. of 2'-acetyl-8,8a-deoxy-8,8a-dihydro-oleandomycin in 500 ml. of toluene is added. After stirring for 2 hrs. at −20° C., 11.4 ml. of triethylamine is added and the reaction mixture gradually allowed to warm to 0° C. It is then poured into 1500 ml. of water and the pH adjusted to 9.5 with 1N sodium hydroxide solution. The organic layer is separated, washed successively with water (3×) and a saturated brine solution (1×) and dried over sodium sulfate. Removal of the solvent under reduced pressure gives a foam, which on recrystallization from diethyl ether provides 13 g. of the pure product, m.p. 197°–199° C.

NMR ($\delta$, $CDCl_3$): 5.11 (1H)m, 3.51 (3H)s, 2.25 (6H)s and 2.03 (3H)s.

EXAMPLE 7

8,8a-Deoxy-8,8a-dihydro-4"-deoxy-4"-oxo-oleandomycin

A suspension of 2.0 g. of 2'-acetyl-8,8a-deoxy-8,8a-dihydro-4"-deoxy-4"-oxo-oleandomycin in 100 ml. of methanol is allowed to stir at room temperature for 20 hrs. The reaction mixture is concentrated under reduced pressure to provide 1.8 g. of the desired product as a white foam.

NMR (δ, CDCl₃): 5.30 (1H)m, 3.51 (3H)s and 2.26 (6H)s.

EXAMPLE 8

11,2'-Diacetyl-8,8a-deoxy-8,8a-dihydro-4"-deoxy-4"-oxo-oleandomycin

To a suspension of 13.0 g. of 2'-acetyl-8,8a-deoxy-8,8a-dihydro-4"-deoxy-4"-oxo-oleandomycin in 65.0 ml. of acetic anhydride cooled in an ice bath is added 2.8 ml. of pyridine. The bath is removed and the reaction mixture allowed to stir at room temperature overnight. The resulting solution is subsequently added to 500 ml. of water and 300 ml. of ethyl acetate. The pH is adjusted to 7.0 with solid sodium bicarbonate and then to 9.5 with 4N aqueous sodium hydroxide. The organic layer is separated, washed with water (2×) and brine solution (1×), and dried over sodium sulfate. Removal of the solvent in vacuo gives the crude product as a foam.

Since chromatography results on the crude sample suggest incompleteness of reaction, the crude foam is recombined with 28 ml. of pyridine and 79 ml. of acetic anhydride and allowed to stir at room temperature for 72 hrs. The reaction mixture is worked up as above to give 12.4 g. of the desired product.

NMR (δ, CDCl₃): 3.51 (3H)s, 2.26 (6H)s and 2.10 (6H)s.

EXAMPLE 9

11-Propionyl-2'-acetyl-8,8a-deoxy-8,8a-dihydro-4"-deoxy-4"-oxo-oleandomycin

The procedure of Example 8 is repeated starting with 6.5 g. of 2'-acetyl-8,8a-deoxy-8,8a-dihydro-4"-deoxy-4"-oxo-oleandomycin, 40 ml. of propionic anhydride and 14 ml. of pyridine. After a reaction time of 72 hrs., the mixture is worked up as indicated in Example 8 to provide the desired product.

EXAMPLE 10

11-Acetyl-8,8a-deoxy-8,8a-dihydro-4"-deoxy-4"-oxo-oleandomycin

A solution of 11.5 g. of 11,2'-diacetyl-8,8a-deoxy-8,8a-dihydro-4"-deoxy-4"-oxo-oleandomycin in 100 ml. of methanol is allowed to stir overnight at room temperature. Concentration of the reaction mixture to dryness under reduced pressure gives 10.6 g. of the crude product as a foam. The crude material is dissolved in chloroform and placed on a silica gel column. After 3 l. of chloroform has passed through the column, the product is eluted with chloroform/methanol (19:1). Eight hundred drop fractions are taken on an automatic fraction collector. Fractions 50-56, 57-62, 63-69 and 70-80 are combined and concentrated in vacuo to dryness to give 2.9 g. of the pure product.

NMR (δ, CDCl₃): 3.55 (3H)s, 2.31 (6H)s and 2.05 (3H)s.

EXAMPLE 11

11-Propionyl-8,8a-deoxy-8,8a-dihydro-4"-deoxy-4"-oxo-oleandomycin

Starting with 11-propionyl-2'-acetyl-8,8a-deoxy-8,8a-dihydro-4"-deoxy-4"-oxo-oleandomycin of Example 9 and following the procedure of Example 10, the desired compound is prepared.

EXAMPLE 12

2'-Acetyl-8,8a-deoxy-8,8a-dihydro-oleandomycin

To a solution of 5.0 g. of 8,8a-deoxy-8,8a-dihydro-oleandomycin in 15 ml. of benzene is added 0.73 ml. of acetic anhydride and the resulting reaction mixture allowed to stir at ambient temperature for 1.5 hrs. The solution is added to 100 ml. of water and the pH adjusted to 7.5 with solid sodium bicarbonate and then 9.5 with 1N aqueous sodium hydroxide. After 10 min. stirring the organic layer is separated, washed successively with water (2×) and a saturated brine solution (1×) and then dried over sodium sulfate. Removal of the solvent under reduced pressure gives 4.9 g. of the desired product, m.p. 202°-204° C.

NMR (δ, CDCl₃): 5.05 (1H)m, 3.40 (3H)s, 2.25 (6H)s and 2.05 (3H)s.

Similarly, by replacing the acetic anhydride with an equivalent amount of propionic anhydride, 2'-propionyl-8,8a-deoxy-8,8a-dihydro-oleandomycin is prepared.

EXAMPLE 13

2'-Propionyl-8,8a-deoxy-8,8a-dihydro-4"-deoxy-4"-oxo-oleandomycin

To a solution of 375 ml. of toluene and 125 ml. of benzene is added 5.8 g. of N-chlorosuccinimide and the mixture allowed to stir at room temperature for 15 min. The reaction mixture is cooled to −5° C. and 3.0 ml. of dimethyl sulfide is added, and stirring continued for an additional 20 min. The temperature is lowered to −20° C. followed by the addition of 12.8 g. of 2'-propionyl-8,8a-deoxy-8,8a-dihydro-oleandomycin in 250 ml. of toluene. After 2 hrs., 5.7 ml. of diethylamine is added and the cooling bath removed. When the reaction temperature reaches 0° C., the mixture is quenched in 750 ml. of water. The pH is adjusted to 9.5 with 1N sodium hydroxide solution and the organic layer separated. After washing with water (3×) and a saturated brine solution, the organic layer is dried and concentrated under reduced pressure to give the desired product.

EXAMPLE 14

11,2'-Diacetyl-8,8a-deoxy-8,8a-methylene-4"-deoxy-4"-oxo-oleandomycin

To a turbid solution of 434 mg. of N-chlorosuccinimide in 15 ml. of toluene and 5 ml. of benzene cooled to −5° C. is added 0.327 ml. of dimethylsulfide. After stirring for 20 min. at 0° C., the reaction mixture is cooled to −25° C. and 500 mg. of 11,2'-diacetyl-8,8a-deoxy-8,8a-methylene-oleandomycin and 10 ml. of toluene are added. Stirring is continued for 2 hrs. at −20° C. followed by the addition of 0.46 ml. triethylamine and 1 ml. of toluene. The cooling bath is removed and the reaction mixture allowed to warm to 0° C. It is then poured into 50 ml. of water and 50 ml. of ethyl acetate. The pH is carefully adjusted to 9.5 and the organic layer separated, dried and concentrated to dryness. In this manner 520 mg. of the slightly wet desired product is obtained as a white foam.

NMR (δ, CDCl₃): 3.50 (3H)s, 2.30 (6H)s, 2.06 (6H)s and 0.58 (4H)m.

EXAMPLE 15

Starting with the appropriate 8,8a-deoxy-8,8a-methylene-oleandomycin and employing the procedure of Example 14, the following 8,8a-deoxy-8,8a-methylene-4"-deoxy-4"-oxo-oleandomycin derivatives are prepared:

| R | R₁ |
|---|---|
| $\underset{\text{O}}{\overset{\text{O}}{\underset{\|}{\text{CH}_3\text{C}—}}}$ | $\underset{\|}{\overset{\text{O}}{\text{CH}_3\text{CH}_2\text{C}—}}$ |
| $\text{CH}_3\text{CH}_2\overset{\text{O}}{\underset{\|}{\text{C}}}—$ | $\text{CH}_3\overset{\text{O}}{\underset{\|}{\text{C}}}—$ |
| $\text{CH}_3\text{CH}_2\overset{\text{O}}{\underset{\|}{\text{C}}}—$ | $\text{CH}_3\text{CH}_2\overset{\text{O}}{\underset{\|}{\text{C}}}—$ |
| H— | $\text{CH}_3\overset{\text{O}}{\underset{\|}{\text{C}}}—$ |
| H— | $\text{CH}_3\text{CH}_2\overset{\text{O}}{\underset{\|}{\text{C}}}—$ |

EXAMPLE 16

11-Acetyl-8,8a-deoxy-8,8a-methylene-4"-deoxy-4"-oxo-oleandomycin

A solution of 400 mg. of 11,2'-diacetyl-8,8a-deoxy-8,8a-methylene-4"-deoxy-4"-oxo-oleandomycin in 10 ml. of methanol, after stirring at room temperature overnight, is concentrated under vacuum to give 270 mg. of the desired product.

NMR (δ, CDCl₃): 3.46 (3H)s, 2.26 (6H)s, 2.03 (3H)s and 0.56 (4H)m.

EXAMPLE 17

The procedure of Example 16 is repeated starting with the appropriate 2'-alkanoyl-8,8a-deoxy-8,8a-methylene-4"-deoxy-4"-oxo-oleandomycin to provide the following compounds:

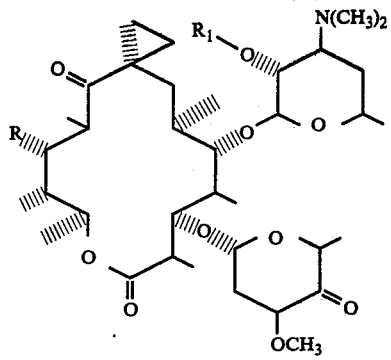

| Starting Material | | Product | |
|---|---|---|---|
| R | R₁ | R | R₁ |
| $\text{CH}_3\overset{\text{O}}{\underset{\|}{\text{C}}}—$ | $\text{CH}_3\text{CH}_2\overset{\text{O}}{\underset{\|}{\text{C}}}—$ | $\text{CH}_3\overset{\text{O}}{\underset{\|}{\text{C}}}—$ | H— |
| $\text{CH}_3\text{CH}_2\overset{\text{O}}{\underset{\|}{\text{C}}}—$ | $\text{CH}_3\overset{\text{O}}{\underset{\|}{\text{C}}}—$ | $\text{CH}_3\text{CH}_2\overset{\text{O}}{\underset{\|}{\text{C}}}—$ | H— |
| $\text{CH}_3\text{CH}_2\overset{\text{O}}{\underset{\|}{\text{C}}}—$ | $\text{CH}_3\text{CH}_2\overset{\text{O}}{\underset{\|}{\text{C}}}—$ | $\text{CH}_3\text{CH}_2\overset{\text{O}}{\underset{\|}{\text{C}}}$ | H— |
| H— | $\text{CH}_3\overset{\text{O}}{\underset{\|}{\text{C}}}—$ | H— | H— |
| H— | $\text{CH}_3\text{CH}_2\overset{\text{O}}{\underset{\|}{\text{C}}}—$ | H— | H— |

EXAMPLE 18

11,2'-Diacetyl-8,8a-deoxy-8,8a-methylene-4"-deoxy-4"-oxo-oleandomycin

In a dry flask equipped with a nitrogen inlet is introduced 18 ml. of methylene dichloride and 1.97 ml. of dimethylsulfoxide, and the resulting solution cooled to −60° C. Trifluoroacetic anhydride (3.9 ml.) is gradually added and stirring continued in the cold for 10 min. The reaction mixture is further cooled to −70° C. and 5.34 g. of 11,2'-diacetyl-8,8a-deoxy-8,8a-methylene-oleandomycin in 27 ml. of methylene dichloride is added dropwise at such a rate that the temperature does not rise above −50° C. After the reaction mixture is cooled back to −70° C., 9.69 ml. of triethylamine is added and cooling continued for 10 min. The reaction is allowed to warm to −10° C., and is then poured into 75 ml. of water. The pH is adjusted to 9.5 with 1N sodium hydroxide solution and the methylene dichloride separated. The organic layer is subsequently washed with water (2 × 30) and a saturated brine solution (1 × 20) and dried over sodium sulfate. Removal of the solvent in vacuo gives 6.2 g. of product which, except for a trace amount of impurities, is identical with the product of Example 14.

EXAMPLE 19

The procedure of Example 18 is repeated, starting with the requisite 2'-alkanoyl-8,8a-deoxy-8,8a-methylene-oleandomycin, to give the following 4"-deoxy-4"-oxo derivatives:

| R | R₁ |
|---|---|
| CH₃CH₂C(O)− | CH₃C(O)− |
| H− | CH₃C(O)− |
| H− | CH₃CH₂C(O)− |
| CH₃C(O)− | CH₃CH₂C(O)− |
| CH₃CH₂C(O)− | CH₃CH₂C(O)− |

EXAMPLE 20

11,2'-Diacetyl-4''-deoxy-4''-oxo-oleandomycin oxime

To a solution of 18.1 g. of hydroxylamine hydrochloride in 300 ml. of water and 200 ml. of methanol is added 50 g. of 11,2'-diacetyl-4''-deoxy-4''-oxo-oleandomycin and the reaction mixture allowed to stir at room temperature for 1 hour. The resulting solution is added to water and the pH subsequently adjusted to 7.5 with solid sodium bicarbonate and then 9.5 with 1N sodium hydroxide. The product is extracted into ethyl acetate and the dried extracts concentrated to about 170 ml. Hexane is added to the heated ethyl acetate solution to the cloud point and the hazy solution cooled. The precipitated product is filtered and dried, 29.8 g., m.p. 223.5°–225° C.

NMR (δ, CDCl₃): 3.30 (3H)s, 2.65 (2H)m, 2.35 (6H)s and 2.10 (3H)s.

In a similar manner, by starting with O-acetylhydroxylamine hydrochloride and the requisite ketone and following the above procedure there is obtained 2'-acetyl-4''-deoxy-4''-oxo-oleandomycin O-acetyloxime and 2'-propionyl-4''-deoxy-4''-oxo-oleandomycin O-acetyloxime.

EXAMPLE 21

The procedure of Example 20 is repeated, starting with the appropriate 4''-deoxy-4''-oxo-oleandomycin, to give the following oximes:

| R | R₁ |
|---|---|
| H− | CH₃C(O)− |
| H− | CH₃CH₂C(O)− |
| CH₃C(O)− | CH₃CH₂C(O)− |
| CH₃CH₂C(O)− | CH₃C(O)− |
| CH₃CH₂C(O)− | CH₃CH₂C(O)− |
| CH₃C(O)− | H− |
| CH₃CH₂C(O)− | H− |
| H− | H− |

EXAMPLE 22

11-Acetyl-4''-deoxy-4''-oxo-oleandomycin oxime

A solution of 500 mg. of 11,2'-diacetyl-4''-deoxy-4''-oxo-oleandomycin oxime in 100 ml. of methanol, after stirring 72 hrs. at room temperature, is concentrated to dryness under reduced pressure. The resulting foam is recrystallized from ethyl acetate-hexane, 372 mg., m.p. 184°–186° C.

NMR (δ, CDCl₃): 3.30 (3H)s, 2.66 (2H)m, 2.36 (6H)s and 2.10 (3H)s.

EXAMPLE 23

Starting with the requisite oxime and employing the procedure of Example 22, the following compounds are prepared:

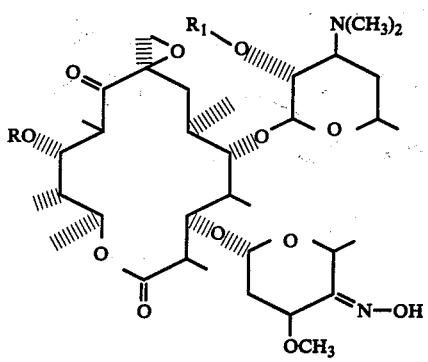

| Starting Material | | Product | |
|---|---|---|---|
| R | $R_1$ | R | $R_1$ |
| H— | $CH_3\overset{O}{\overset{\|}{C}}$— | H— | H— |
| H— | $CH_3CH_2\overset{O}{\overset{\|}{C}}$— | H— | H— |
| $CH_3\overset{O}{\overset{\|}{C}}$— | $CH_3CH_2\overset{O}{\overset{\|}{C}}$— | $CH_3\overset{O}{\overset{\|}{C}}$— | H— |
| $CH_3CH_2\overset{O}{\overset{\|}{C}}$— | $CH_3\overset{O}{\overset{\|}{C}}$— | $CH_3CH_2\overset{O}{\overset{\|}{C}}$— | H— |
| $CH_3CH_2\overset{O}{\overset{\|}{C}}$— | $CH_3CH_2\overset{O}{\overset{\|}{C}}$— | $CH_3CH_2\overset{O}{\overset{\|}{C}}$— | H— |

EXAMPLE 24

11,2′-Diacetyl-4″-deoxy-4″-oxo-oleandomycin O-acetyloxime

To a stirring turbid solution of 20 g. of 11,2′-diacetyl-4″-deoxy-4″-oxo-oleandomycin oxime in 250 ml. of benzene is added 8.21 ml. of pyridine followed by 9.62 ml. of acetic anhydride, and the resulting reaction mixture allowed to stir at room temperature overnight. The solution is poured into water and the organic layer, after washing successively with water and a saturated brine solution and drying, is concentrated to dryness. Recrystallization of the residual foam from ethyl acetate-hexane gave 13.4 g. of the pure product, m.p. 198°–202° C.

NMR (δ, CDCl₃): 3.38 (3H)s, 2.66 (2H)m, 2.33 (6H)s, 2.26 (3H)s and 2.10 (6H)s.

EXAMPLE 25

The procedure of Example 24 is again repeated, starting with the appropriate oxime, to give the following products:

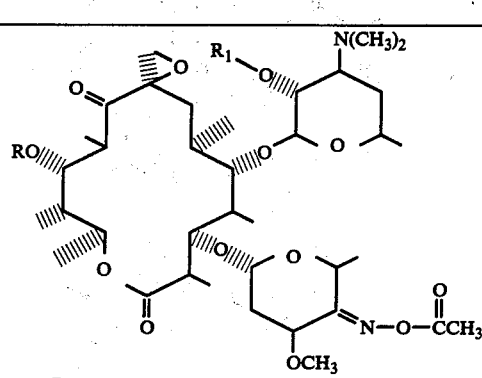

| R | $R_1$ |
|---|---|
| $CH_3\overset{O}{\overset{\|}{C}}$— | $CH_3CH_2\overset{O}{\overset{\|}{C}}$— |
| $CH_3CH_2\overset{O}{\overset{\|}{C}}$— | $CH_3\overset{O}{\overset{\|}{C}}$— |
| $CH_3\overset{O}{\overset{\|}{C}}$— | H— |
| $CH_3CH_2\overset{O}{\overset{\|}{C}}$— | H— |

EXAMPLE 26

11,2′-Diacetyl-4″-deoxy-4″-oxo-oleandomycin O-methyloxime

To 50 ml. of water and 50 ml. of methanol is added 1.25 g. of methoxyamine hydrochloride and 2.5 g. of 11,2′-diacetyl-4″-deoxy-4″-oxo-oleandomycin and the resulting reaction mixture allowed to stir at room temperature overnight. The solution is added to water and the pH adjusted to 7.5 with solid sodium bicarbonate and then 9.5 with 1N aqueous sodium hydroxide solution. The product is extracted into ethyl acetate and the extract dried over sodium sulfate. Removal of the solvent in vacuo gives 2.4 g. of the desired product as a white foam.

NMR (δ, CDCl₃): 3.88 (3H)s, 3.26 (3H)s, 2.56 (2H)m, 2.30 (6H)s and 2.06 (6H)s.

EXAMPLE 27

Employing the procedure of Example 26 and starting with methoxyamine hydrochloride and the requisite 4″-deoxy-4″-oxo-oleandomycin, the following compounds are prepared: 2′-acetyl-4″-deoxy-4″-oxo-oleandomycin O-methyloxime, 2′-propionyl-4″-deoxy-4″-oxo-oleandomycin O-methyloxime, 11-acetyl-2′-propionyl-4″-deoxy-4″-oxo-oleandomycin O-methyloxime, 11-propionyl-2′-acetyl-4″-oxo-oleandomycin O-methyloxime, 11-acetyl-4″-deoxy-4″-oxo-oleandomycin O-methyloxime and 11-propionyl-4″-deoxy-4″-oxo-oleandomycin O-methyloxime.

EXAMPLE 28

11,2′-Diacetyl-8,8a-deoxy-8,8a-dihydro-4″-deoxy-4″-oxo-oleandomycin oxime

A solution of 49.0 g. of 11,2′-diacetyl-8,8a-deoxy-8,8a-dihydro-4″-deoxy-4″-oxo-oleandomycin and 18.1 g. of hydroxylamine hydrochloride in 300 ml. of water and 300 ml. of methanol is allowed to stir at room temperature for 1.5 hrs. The resulting solution is added to 250 ml. of water and the pH adjusted to 7.5 and 9.5 with solid sodium bicarbonate and 1N sodium hydroxide solution, respectively. The product is extracted with ethyl acetate, which is then dried over sodium sulfate and concentrated to dryness. Recrystallization of the residue from ethyl acetate-hexane gives the desired product.

EXAMPLE 29

Employing the procedure of Example 28 and starting with the appropriate 4"-deoxy-4"-oxo-oleandomycin and requisite hydroxylamine derivatives, the following compounds are prepared:

[Structure diagram of oleandomycin derivative with substituents R, R₁, and X shown on macrolide core with N(CH₃)₂ and OCH₃ groups]

| R | R₁ | X |
|---|---|---|
| H— | $\underset{\text{CH}_3\text{C}-}{\overset{\text{O}}{\underset{\|}{\|}}}$ | N—OH |
| $\underset{\text{CH}_3\text{CH}_2\text{C}-}{\overset{\text{O}}{\|}}$ | $\underset{\text{CH}_3\text{C}-}{\overset{\text{O}}{\|}}$ | N—OH |
| $\underset{\text{CH}_3\text{C}-}{\overset{\text{O}}{\|}}$ | H— | N—OH |
| $\underset{\text{CH}_3\text{CH}_2\text{C}-}{\overset{\text{O}}{\|}}$ | H— | N—OH |
| H— | $\underset{\text{CH}_3\text{CH}_2\text{C}-}{\overset{\text{O}}{\|}}$ | N—OH |
| $\underset{\text{CH}_3\text{CH}_2\text{C}-}{\overset{\text{O}}{\|}}$ | $\underset{\text{CH}_3\text{C}-}{\overset{\text{O}}{\|}}$ | N—OCH₃ |
| $\underset{\text{CH}_3\text{C}-}{\overset{\text{O}}{\|}}$ | $\underset{\text{CH}_3\text{C}-}{\overset{\text{O}}{\|}}$ | N—OCH₃ |
| H— | $\underset{\text{CH}_3\text{C}-}{\overset{\text{O}}{\|}}$ | N—OCH₃ |
| $\underset{\text{CH}_3\text{C}-}{\overset{\text{O}}{\|}}$ | H— | N—OCH₃ |
| $\underset{\text{CH}_3\text{CH}_2\text{C}-}{\overset{\text{O}}{\|}}$ | H— | N—OCH₃ |

EXAMPLE 30

11,2'-Diacetyl-8,8a-deoxy-8,8a-dihydro-4"-deoxy-4"-oxo-oleandomycin O-acetyloxime To a solution of 9.9 g. of 11,2'-diacetyl-8,8a-deoxy-8,8a-dihydro-4"-deoxy-4"-oxo-oleandomycin oxime and 4.1 ml. of pyridine in 125 ml. of benzene is added 4.81 ml. of acetic anhydride and the resulting reaction mixture allowed to stir at room temperature overnight. The reaction is poured into water and the pH adjusted to 7.5 and 9.5 with solid sodium bicarbonate and 1N sodium hydroxide, respectively. The benzene layer is separated, dried over sodium sulfate and concentrated to give the desired product as a white foam.

EXAMPLE 31

The procedure of Example 30 is repeated, starting with the appropriate oxime, to give the following compounds: 2'-acetyl-8,8a-deoxy-8,8a-dihydro-4"-deoxy-4"-oxo-oleandomycin O-acetyloxime, 11-propionyl-2'-acetyl-8,8a-deoxy-8,8a-dihydro-4"-deoxy-4"-oxo-oleandomycin O-acetyloxime, 11-propionyl-8,8a-deoxy-8,8a-dihydro-4"-deoxy-4"-oxo-oleandomycin O-acetyloxime, 2'-propionyl-8,8a-deoxy-8,8a-dihydro-4"-deoxy-4"-oxo-oleandomycin O-acetyloxime and 11-acetyl-8,8a-deoxy-8,8a-dihydro-4"-deoxy-4"-oxo-oleandomycin O-acetyloxime.

EXAMPLE 32

11-Propionyl-8,8a-deoxy-8,8a-dihydro-4"-deoxy-4"-oxo-oleandomycin oxime

A solution of 500 mg. of 11-propionyl-2'-acetyl-8,8a-deoxy-8,8a-dihydro-4"-deoxy-4"-oxo-oleandomycin oxime in 100 ml. of methanol is allowed to stir at room temperature overnight. The solution is concentrated to dryness and the residual foam purified by recrystallization from ethyl acetate-hexane.

In a similar manner is prepared 8,8a-deoxy-8,8a-dihydro-4"-deoxy-4"-oxo-oleandomycin oxime from 2'-acetyl-8,8a-deoxy-8,8a-dihydro-4"-deoxy-4"-oxo-oleandomycin oxime.

EXAMPLE 33

11,2'-Diacetyl-8,8a-deoxy-8,8a-methylene-4"-deoxy-4"-oxo-oleandomycin O-methyloxime A solution of 90 mg. of 11,2'-diacetyl-8,8a-deoxy-8,8a-methylene-4"-deoxy-4"-oxo-oleandomycin and 45 mg. of methoxyamine hydrochloride in 2 ml. of water and 2 ml. of methanol is allowed to stir at room temperature overnight. The solution is poured into water and the pH adjusted to 7.5 and 9.5 with solid sodium bicarbonate and 1N sodium hydroxide, respectively. The product is extracted with ethyl acetate and the organic layer subsequently dried and concentrated to give 89.2 mg. of the desired product.

NMR (δ, CDCl₃): 5.56 (3H)s, 3.33 (1.5H)s, 3.26 (1.5H)s, 2.28 (6H)s, 2.06 (6H)s and 0.56 (4H)m.

EXAMPLE 34

11,2'-Diacetyl-8,8a-deoxy-8,8a-methylene-4"-deoxy-4"-oxo-oleandomycin oxime

The procedure of Example 33 is repeated employing 10.0 g. of 11,2'-diacetyl-8,8a-deoxy-8,8a-methylene-4"-deoxy-4"-oxo-oleandomycin, 3.4 g. of hydroxylamine hydrochloride, 50 ml. of methanol and 50 ml. of water to give on work-up 9.2 g. of the desired product which can be further purified by recrystallization from ethyl acetate, m.p. 177°–180° C.

NMR (δ, CDCl₃): 3.35 (1.5H)s, 3.25 (1.5H)s, 2.33 (6H)s, 2.06 (6H)s and 0.53 (4H)m.

EXAMPLE 35

Employing the procedure of Example 33 and starting with the requisite hydroxylamine hydrochloride and appropriate 8,8a-deoxy-8,8a-methylene-4"-deoxy-4"-oxo-oleandomycin, the following compounds are synthesized:

| R | R₁ | X |
|---|---|---|
| CH₃C(O)— | CH₃CH₂C(O)— | N—OH |
| CH₃CH₂C(O)— | CH₃C(O)— | N—OH |
| CH₃CH₂C(O)— | CH₃CH₂C(O)— | N—OH |
| H— | CH₃C(O)— | N—OH |
| H— | CH₃CH₂C(O)— | N—OH |
| CH₃C(O)— | H— | N—OH |
| CH₃CH₂C(O)— | CH₃C(O)— | N—OCH₃ |
| CH₃CH₂C(O)— | CH₃CH₂C(O)— | N—OCH₃ |
| H— | CH₃C(O)— | N—OCH₃ |
| CH₃C(O)— | H— | N—OCH₃ |

EXAMPLE 36

11,2'-Diacetyl-8,8a-deoxy-8,8a-methylene-4"-deoxy-4"-oxo-oleandomycin O-acetyloxime To a suspension of 1.0 g. of 11,2'-diacetyl-8,8a-deoxy-8,8a-methylene-4"-deoxy-4"-oxo-oleandomycin oxime in 10 ml. of benzene is added 0.18 ml. of pyridine followed by 0.24 ml. of acetic anhydride. After 2 hrs. of stirring at room temperature an additional 0.09 ml. of pyridine and 0.12 ml. of acetic anhydride are added and the stirring continued overnight. The reaction mixture is poured into water and the pH adjusted to 7.5 then 9.5 by the addition of solid sodium bicarbonate and 1N sodium hydroxide, respectively. The benzene layer is separated, dried over sodium sulfate and concentrated under vacuum to dryness to give 890 mg. of the desired product.

NMR (δ, CDCl₃): 3.31 (1.5H)s, 3.25 (1.5H)s, 2.25 (6H)s, 2.16 (3H)s, 2.01 (6H)s and 0.55 (4H)m.

Similarly the oximes of Example 35 are converted to their O-acetyl derivatives.

EXAMPLE 37

11-Acetyl-4"-deoxy-4"-amino-oleandomycin

To a suspension of 10 g. of 10% palladium-on-charcoal in 100 ml. of methanol is added 21.2 g. of ammonium acetate and the resulting slurry is treated with a solution of 20 g. of 11-acetyl-4"-deoxy-4"-oxo-oleandomycin in 100 ml. of the same solvent. The suspension is shaken at room temperature in a hydrogen atmosphere at an initial pressure of 50 p.s.i. After 1.5 hrs., the catalyst is filtered and the filtrate is added with stirring to a mixture of 1200 ml. of water and 500 ml. of chloroform. The pH is adjusted from 6.4 to 4.5 and the organic layer is separated. The aqueous layer, after a further extraction with 500 ml. of chloroform, is treated with 500 ml. of ethyl acetate and the pH adjusted to 9.5 with 1N sodium hydroxide. The ethyl acetate layer is separated and the aqueous layer extracted again with ethyl acetate. The ethyl acetate extracts are combined, dried over sodium sulfate and concentrated to a yellow foam (18.6 g.), which on crystallization from diisopropyl ether, provides 6.85 g. of the purified product, m.p. 157.5°–160° C.

NMR (δ, CDCl₃): 3.41 (3H)s, 2.70 (2H)m, 2.36 (6H)s and 2.10 (3H)s.

The other epimer, which exists in the crude foam to the extent of 20–25%, is obtained by gradual concentration and filtration of the mother liquors.

EXAMPLE 38

Employing the procedure of Example 37 and starting with the appropriate 4"-deoxy-4"-oxo-oleandomycin and alcohol solvent, the following amines are prepared:

| R | R₁ | NMR (δ, CDCl₃) |
|---|---|---|
| CH₃C(O)— | CH₃C(O)— | 3.43 (3H)s, 2.70 (2H)m, 2.30 (6H)s and 2.10 (6H)s. |
| H— | H— | 5.60 (1H)m, 3.36 (3H)s, 2.83 (2H)m and 2.30 (6H)s. |
| H— | CH₃C(O)— | 5.80 (1H)m, 3.43 (3H)s, 2.80 (2H)m, 2.30 (6H)s and 2.10 (3H)s. |

EXAMPLE 39

The procedure of Example 37 is again repeated starting with the requisite 4"-deoxy-4"-oxo-oleandomycin and using isopropanol as the solvent to give the following products: 2'-propionyl-4"-deoxy-4"-amino-oleandomycin, 11-acetyl-2'-propionyl-4"-deoxy-4"-amino-oleandomycin, 11-propionyl-2'-acetyl-4"-deoxy-4"-amino-oleandomycin and 11,2'-dipropionyl-4"-deoxy-4"-oxo-oleandomycin.

EXAMPLE 40

11-Acetyl-4"-deoxy-4"-amino-oleandomycin

To a stirred suspension of 50 g. of 11-acetyl-4"-deoxy-4"-oxo-oleandomycin and 53 g. of ammonium acetate in 500 ml. of methanol cooled to −10° C. is added dropwise over a 1 hour period a solution of 3.7 g. of 85% sodium borocyanohydride in 200 ml. of methanol. After stirring for 2 hrs. in the cold, the reaction is poured into 2.5 l. of water and 1 l. of chloroform. The pH is adjusted from 7.2 to 9.5 by the addition of 1N sodium hydroxide and the organic layer separated. The aqueous layer is washed once with chloroform and the organic layer combined. The chloroform solution of the product is treated with 1.5 l. of water at pH 2.5, and the water layer separated. The pH of the aqueous layer is adjusted from 2.5 to 7.5 and then to 8.25 and is followed by an ethyl acetate extraction. These extracts are discarded and the pH is finally raised to 9.9. The aqueous layer is extracted (2 × 825 ml.) with ethyl acetate and the extracts combined and dried over sodium sulfate. Removal of the solvent under reduced pressure gives 23.9 g. of the product as a foam.

NMR ($\delta$, CDCl$_3$): 3.41 (3H)s, 2.70 (2H)m, 2.36 (6H)s and 2.10 (3H)s.

EXAMPLE 41

4″-Deoxy-4″-amino-oleandomycin

A solution of 20 g. of 2′-acetyl-4″-deoxy-4″-oxo-oleandomycin in 125 ml. of methanol, after stirring at room temperature overnight, is treated with 21.2 g. of ammonium acetate. The resulting solution is cooled in an ice bath and treated with 1.26 g. of sodium cyanoborohydride. The cooling bath is then removed and the reaction mixture allowed to stir at room temperature for 2 hrs. The reaction is poured into 600 ml. of water and 600 ml. of diethyl ether and the pH adjusted from 8.3 to 7.5. The ether layer is separated and the aqueous extracted with ethyl acetate. The extracts are set aside and the pH of the aqueous adjusted to 8.25. The diethyl ether and ethyl acetate extracts made at this pH are also set aside, and the pH raised to 9.9. The diethyl ether and ethyl acetate extracts at this pH are combined, washed successively with water (1×) and a saturated brine solution and dried over sodium sulfate. The latter extracts, taken at pH 9.9, are concentrated to a foam and chromatographed on 160 g. of silica gel, using chloroform as the loading solvent and initial eluate. After eleven fraction, which amounts to 12 ml. per fraction, are taken, the eluate is changed to 5% methanol–95% chloroform. At fraction 370 the eluate is changed to 10% methanol–90% chloroform and at fraction 440, 15% methanol–85% chloroform is used. Fractions 85–260 are combined and concentrated in vacuo to dryness to provide 2.44 g. of the desired product.

NMR ($\delta$, CDCl$_3$): 5.56 (1H)m, 3.36 (3H)s, 2.9 (2H)m and 2.26 (6H)s.

EXAMPLE 42

Employing the procedure of Example 40 and starting with the appropriate 4″-deoxy-4″-oxo-oleandomycin and using isopropanol as the solvent, the following compounds are prepared: 11,2′-diacetyl-4″-deoxy-4″-amino-oleandomycin, 2′-propionyl-4″-deoxy-4″-amino-oleandomycin, 2′-acetyl-4″-deoxy-4″-aminooleandomycin, 11-acetyl-2′-propionyl-4″-deoxy-4″-amino-oleandomycin, 11-propionyl-2′-acetyl-4″-deoxy-4″-amino-oleandomycin and 11,2′-dipropionyl-4″-deoxy-4″-amino-oleandomycin.

EXAMPLE 43

4″-Deoxy-4″-amino-oleandomycin

A solution of 300 mg. of 2′-acetyl-4″-deoxy-4″-amino-oleandomycin in 25 ml. of methanol is allowed to stir under a nitrogen atmosphere overnight at room temperature. The reaction mixture is concentrated in vacuo to give 286 mg. of the desired product as a white foam.

NMR ($\delta$, CDCl$_3$): 5.56 (1H)m, 3.36 (3H)s, 2.90 (2H)m and 2.26 (6H)s.

EXAMPLE 44

The procedure of Example 43 is repeated, starting with the requisite 2′-alkanoyl-4″-deoxy-4″-amino-oleandomycin, to give the following compounds:

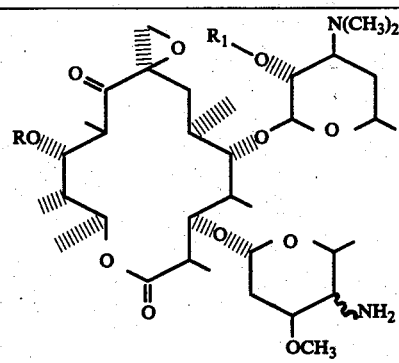

| Starting Material | | Product | |
|---|---|---|---|
| R | R$_1$ | R | R$_1$ |
| CH$_3$C(O)— | CH$_3$C(O)— | CH$_3$C(O)— | H— |
| CH$_3$C(O)— | CH$_3$CH$_2$C(O)— | CH$_3$C(O)— | H— |
| CH$_3$CH$_2$C(O)— | CH$_3$C(O)— | CH$_3$CH$_2$C(O)— | H— |
| CH$_3$CH$_2$C(O)— | CH$_3$CH$_2$C(O)— | CH$_3$CH$_2$C(O)— | H— |
| H— | CH$_3$CH$_2$C(O)— | H— | H— |

EXAMPLE 45

11-Acetyl-8,8a-deoxy-8,8a-dihydro-4″-deoxy-4″-amino-oleandomycin

A solution of 2.15 g. of 11-acetyl-8,8a-deoxy-8,8a-dihydro-4″-deoxy-4″-oxo-oleandomycin and 2.31 g. of ammonium acetate in 15 ml. of methanol cooled to 20° C. is treated with 136 mg. of sodium cyanoborohydride. After stirring for 45 min. at room temperature the reaction mixture is poured into 60 ml. of water and 60 ml. of diethyl ether, and the pH adjusted from 8.1 to 7.5. The ether layer is separated and discarded, and the pH of the aqueous raised to 8.0. Fresh ether is added, shaken with the aqueous layer and discarded. The pH is adjusted to 8.5 and the process repeated. Finally, the pH is adjusted to 10.0 and 60 ml. of ethyl acetate is added. The aqueous layer is discarded and the ethyl acetate treated with 60 ml. of fresh water. The pH of the water layer is adjusted to 6.0 with 1N hydrochloric acid and the ethyl acetate layer discarded. The aqueous layer is successively extracted at pH 6.5, 7.0, 7.5, 8.0 and 8.5 with ethyl acetate (60 ml.) and the organic extracts set aside. The pH is finally raised to 10.0 and the aqueous extracted with ethyl acetate. The extracts taken at pH 8.0, 8.5 and 10.0 are combined and concentrated under vacuum to give 585 mg. of a white foam, which consists of a pair of 4″-epimers.

NMR (δ, CDCl₃): 3.38 and 3.35 (3H) 2 singlets, 2.31 and 2.28 (6H) 2 singlets and 2.03 (3H).

EXAMPLE 46

8,8a-Deoxy-8,8a-dihydro-4″-deoxy-4″-amino-oleandomycin

Sodium cyanoborohydride (126 mg.) is added to a solution of 1.86 g. of 8,8a-deoxy-8,8a-dihydro-4″-deoxy-4″-oxo-oleandomycin and 2.1 g. of ammonium acetate in 10 ml. of methanol at room temperature. After one hour the reaction mixture is cooled to 0° C. and allowed to stir for 2.5 hrs. The reaction mixture is poured into 60 ml. of water and 60 ml. of diethyl ether and the pH adjusted to 7.5. The ether layer is discarded and the aqueous layer adjusted successively to 8.0 and 8.5 being extracted with ether following each adjustment. The aqueous is finally adjusted to pH 10.0 and is extracted with ethyl acetate. Fresh water is added to the ethyl acetate extracted and the pH adjusted to 6.0. The ethyl acetate layer is discarded and the aqueous layer adjusted successively to pH 6.5, 7.0, 8.0, 8.5 and 10.0, the aqueous layer being extracted after each pH adjustment with ethyl acetate. The ethyl acetate extracts at pH's 7.5, 8.0 and 10.0 are combined and concentrated to a foam which is reconstituted in ethyl acetate and extracted with fresh water at pH 5.5. The acid aqueous layer is successively adjusted, as before, to pH's 6.0, 6.5, 7.0, 7.5, 8.0 and 10.0 being extracted after each adjustment with diethyl ether. The ether extracts at pH 7.5, 8.0 and 10.0 are combined and concentrated to dryness in vacuo to give 166 mg. of the desired product.

NMR (δ, CDCl₃): 5.48 (1H)m, 3.40 (3H)s and 2.30 (6H)s.

EXAMPLE 47

The procedure of Example 45 is repeated, starting with the requisite 8,8a-deoxy-8,8a-dihydro-4″-deoxy-4″-oxo-oleandomycin and using isopropanol as the solvent to give the following compounds:

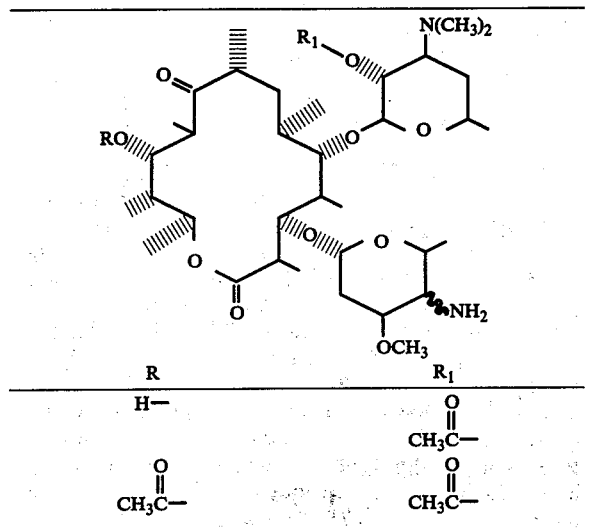

| R | R₁ |
|---|---|
| H— | O<br>‖<br>CH₃C— |
| O<br>‖<br>CH₃C— | O<br>‖<br>CH₃C— |

-continued

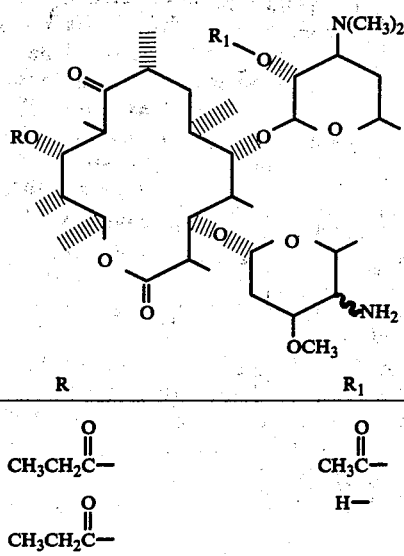

| R | R₁ |
|---|---|
| O<br>‖<br>CH₃CH₂C— | O<br>‖<br>CH₃C— |
| O<br>‖<br>CH₃CH₂C— | H— |

EXAMPLE 48

11-Acetyl-8,8a-deoxy-8,8a-methylene-4″-deoxy-4″-amino-oleandomycin

To a methanol (30 ml.) solution of 5.0 g. of 11-acetyl-8,8a-deoxy-8,8a-methylene-4″-deoxy-4″-oxo-oleandomycin and 5.2 g. of ammonium acetate cooled to 20° C. is added 300 mg. of sodium cyanoborohydride. The reaction mixture is allowed to stir at room temperature for 1 hour, and is then poured into 120 ml. of water and 120 ml. of diethyl ether. The aqueous layer is adjusted to pH 7.5, 8.0, 8.5 and 10.0, successively, being extracted after each pH adjustment with ethyl acetate. The final organic extract made at pH 10.0 is treated with water and the pH adjusted to pH 6. The aqueous layer is treated again as above and the pH adjusted to 7.0, 7.5, 8.0, 8.5 and 10.0, being extracted with ethyl acetate subsequent to the pH change. The ethyl acetate extracts following pH changes at 8.0, 8.5 and 10.0 are combined and concentrated in vacuo to give 1.5 g. of the desired product.

NMR (δ, CDCl₃): 3.38 (3H)s, 2.30 (6H)s, 2.05 (3H)s and 0.65 (4H)m.

EXAMPLE 49

Starting with the appropriate 8,8a-deoxy-8,8a-methylene-4″-deoxy-4″-oxo-oleandomycin and isopropanol as the solvent and employing the procedure of Example 48, the following compounds are synthesized:

| R | R₁ |
|---|---|
| $CH_3\overset{O}{\underset{\|}{C}}-$ | $CH_3\overset{O}{\underset{\|}{C}}-$ |
| $CH_3\overset{O}{\underset{\|}{C}}-$ | $CH_3CH_2\overset{O}{\underset{\|}{C}}-$ |
| $CH_3CH_2\overset{O}{\underset{\|}{C}}-$ | $CH_3\overset{O}{\underset{\|}{C}}-$ |
| $CH_3CH_2\overset{O}{\underset{\|}{C}}-$ | $CH_3CH_2\overset{O}{\underset{\|}{C}}-$ |
| H— | $CH_3\overset{O}{\underset{\|}{C}}-$ |
| H— | $CH_3CH_2\overset{O}{\underset{\|}{C}}-$ |

EXAMPLE 50

11,2′-Diacetyl-4″-deoxy-4″-amino-oleandomycin

A suspension of 1 g. of Raney nickel, washed with isopropanol, in 25 ml. of isopropanol containing 250 mg. of 11,2′-diacetyl-4″-deoxy-4″-oxo-oleandomycin O-acetyloxime is shaken in a hydrogen atmosphere at an initial pressure of 50 p.s.i. at room temperature overnight. The reaction mixture is filtered and the filtrate concentrated under reduced pressure to give 201 mg. of the desired product.

The entire 201 mg. in methanol (10 ml.) is refluxed for 1 hour giving 11-acetyl-4″-deoxy-4″-amino-oleandomycin identical with that prepared in Example 37.

EXAMPLE 51

Starting with the indicated 4″-deoxy-4″-oxo-oleandomycin derivative and employing the procedure of Example 50 with the designated catalyst, the following 4″-deoxy-4″-amino-oleandomycins are prepared:

| R | R₁ | Derivative | Catalyst |
|---|---|---|---|
| $CH_3\overset{O}{\underset{\|}{C}}-$ | $CH_3\overset{O}{\underset{\|}{C}}-$ | oxime | Ni |
| $CH_3\overset{O}{\underset{\|}{C}}-$ | $CH_3CH_2\overset{O}{\underset{\|}{C}}-$ | oxime | Pd/C |
| $CH_3\overset{O}{\underset{\|}{C}}-$ | H— | oxime | PtO₂ |
| $CH_3CH_2\overset{O}{\underset{\|}{C}}-$ | H— | oxime | PtO₂ |
| H— | H— | oxime | Pd/C |
| $CH_3\overset{O}{\underset{\|}{C}}-$ | $CH_3\overset{O}{\underset{\|}{C}}-$ | O-acetyloxime | Ni |
| $CH_3\overset{O}{\underset{\|}{C}}-$ | $CH_3CH_2\overset{O}{\underset{\|}{C}}-$ | O-acetyloxime | Ni |
| H— | $CH_3\overset{O}{\underset{\|}{C}}-$ | O-acetyloxime | Pd/C |
| H— | $CH_3\overset{O}{\underset{\|}{C}}-$ | O-methyloxime | PtO₂ |
| $CH_3\overset{O}{\underset{\|}{C}}-$ | $CH_3CH_2\overset{O}{\underset{\|}{C}}-$ | O-methyloxime | Pd/C |
| $CH_3CH_2\overset{O}{\underset{\|}{C}}-$ | H— | O-methyloxime | Pd/C |

EXAMPLE 52

Employing the procedure of Example 50, 8,8a-deoxy-8,8a-dihydro-4″-deoxy-4″-amino-oleandomycins are prepared which correspond to the reduction products of the following 4″-oxo derivatives using the indicated catalyst:

| R | R₁ | X | Catalyst |
|---|---|---|---|
| H— | $CH_3\overset{O}{\underset{\|}{C}}-$ | N—OH | Pd/C |

-continued

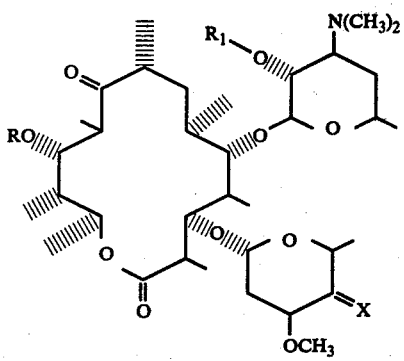

| R | R₁ | X | Catalyst |
|---|---|---|---|
| $CH_3CH_2\overset{O}{\underset{\|}{C}}-$ | $CH_3\overset{O}{\underset{\|}{C}}-$ | N—OH | Ni |
| $CH_3\overset{O}{\underset{\|}{C}}-$ | H— | N—OH | Ni |
| $CH_3CH_2\overset{O}{\underset{\|}{C}}-$ | H— | N—OH | PtO₂ |
| H— | $CH_3CH_2\overset{O}{\underset{\|}{C}}-$ | N—OH | Ni |
| $CH_3CH_2\overset{O}{\underset{\|}{C}}-$ | $CH_3\overset{O}{\underset{\|}{C}}-$ | N—OCH₃ | PtO₂ |
| H— | $CH_3\overset{O}{\underset{\|}{C}}-$ | N—OCH₃ | Pd/C |
| $CH_3\overset{O}{\underset{\|}{C}}-$ | H— | N—OCH₃ | Pd/C |
| $CH_3CH_2\overset{O}{\underset{\|}{C}}-$ | H— | N—OCH₃ | PtO₂ |
| $CH_3\overset{O}{\underset{\|}{C}}-$ | $CH_3\overset{O}{\underset{\|}{C}}-$ | $N-O-\overset{O}{\underset{\|}{C}}CH_3-$ | PtO₂ |
| $CH_3CH_2\overset{O}{\underset{\|}{C}}-$ | $CH_3\overset{O}{\underset{\|}{C}}-$ | $N-O-\overset{O}{\underset{\|}{C}}CH_3-$ | Ni |
| $CH_3CH_2\overset{O}{\underset{\|}{C}}-$ | H— | $N-O-\overset{O}{\underset{\|}{C}}CH_3-$ | Pd/C |
| $CH_3\overset{O}{\underset{\|}{C}}-$ | H— | $N-O-\overset{O}{\underset{\|}{C}}CH_3-$ | Ni |

EXAMPLE 53

The procedure of Example 50 is again repeated, starting with the indicated 8,8a-deoxy-8,8a-methylene-4"-deoxy-4"-oxo-oleandomycin derivative and catalyst to give the following compounds:

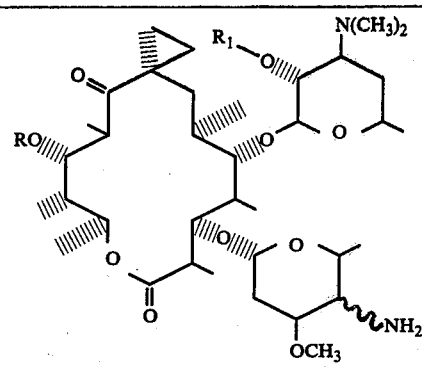

| R | R₁ | Starting Derivative | Catalyst |
|---|---|---|---|
| $CH_3\overset{O}{\underset{\|}{C}}-$ | $CH_3\overset{O}{\underset{\|}{C}}-$ | oxime | Ni |
| $CH_3\overset{O}{\underset{\|}{C}}-$ | $CH_3CH_2\overset{O}{\underset{\|}{C}}-$ | oxime | PtO₂ |
| $CH_3CH_2\overset{O}{\underset{\|}{C}}-$ | $CH_3CH_2\overset{O}{\underset{\|}{C}}-$ | oxime | PtO₂ |
| H— | $CH_3\overset{O}{\underset{\|}{C}}-$ | oxime | Pd/C |
| $CH_3\overset{O}{\underset{\|}{C}}-$ | H— | oxime | PtO₂ |
| $CH_3CH_2\overset{O}{\underset{\|}{C}}-$ | $CH_3\overset{O}{\underset{\|}{C}}-$ | O-methyloxime | Pd/C |
| $CH_3\overset{O}{\underset{\|}{C}}-$ | H— | O-methyloxime | Ni |
| $CH_3\overset{O}{\underset{\|}{C}}-$ | $CH_3\overset{O}{\underset{\|}{C}}-$ | O-acetyloxime | Ni |
| $CH_3\overset{O}{\underset{\|}{C}}-$ | H— | O-acetyloxime | Ni |
| $CH_3\overset{O}{\underset{\|}{C}}-$ | $CH_3\overset{O}{\underset{\|}{C}}-$ | O-acetyloxime | Pd/C |

EXAMPLE 54

4"-Deoxy-4"-ethylamino-oleandomycin

To 25 ml. of methanol containing 4.59 g. of 4"-deoxy-4"-oxo-oleandomycin, 6.6 ml. of a 5 M solution of ethylamine in ethanol and 1.89 ml. of acetic acid is added 365 mg. of sodium cyanoborohydride in 50-60 mg. portions. After stirring at room temperature for 1 hour, the reaction mixture is poured into 110 ml. of water and 120 ml. of ethyl acetate.

The aqueous layer is adjusted to pH 7.5, 8.0, 8.5 and 10.0, successively, being extracted after each pH adjustment with ethyl acetate. The final organic extract made at pH 10.0 is treated with water and the pH adjusted to pH 6. The aqueous layer is treated again as above and the pH adjusted to 7.0, 7.5, 8.0, 8.5 and 10.0, being extracted with ethyl acetate subsequent to the pH change. The ethyl acetate extracts following pH changes at 8.0, 8.5 and 10.0 are combined and concentrated in vacuo to give a foam. The product is further purified by chromatographing on 75 g. of silica gel using acetone eluates. Fractions 62-104, each fraction comprising 4 ml., are combined and concentrated under reduced pressure to give 910 mg. of the desired product.

EXAMPLE 55

11-Acetyl-4''-deoxy-4''-ethylamino-oleandomycin

In a manner similar to Example 54, 366 mg. of sodium cyanoborohydride is added portionwise to a solution of 5.82 g. 11-acetyl-4''-deoxy-4''-oxo-oleandomycin and 16 ml. of a 5.0 solution of ethylamine in ethanol in 27.4 ml. of a 2.92 M solution of hydrogen chloride in ethanol. After stirring at room temperature for 1.5 hrs., the reaction mixture is poured into 120 ml. of water and 120 ml. of ethyl acetate and worked up as in Example 54 to give 1.2 g. of the desired product.

EXAMPLE 56

11-Acetyl-4''-deoxy-4''-n-hexylamino-oleandomycin

The procedure of Example 54 is repeated, starting with 4.8 g. of 11-acetyl-4''-deoxy-4''-oxo-oleandomycin, 6.7 g. of n-hexylamine, 3.78 ml. of acetic acid, 302 mg. of sodium cyanoborohydride and 25 ml. of methanol, to give, after chromatographing an 80 g. of silica gel using chloroform as the eluate, 1.3 g. of the desired product.

EXAMPLE 57

Starting with the appropriate 4''-deoxy-4''-oxo-oleandomycin, isopropanol as the solvent and amine, and employing the procedure of Example 54, the following compounds are prepared:

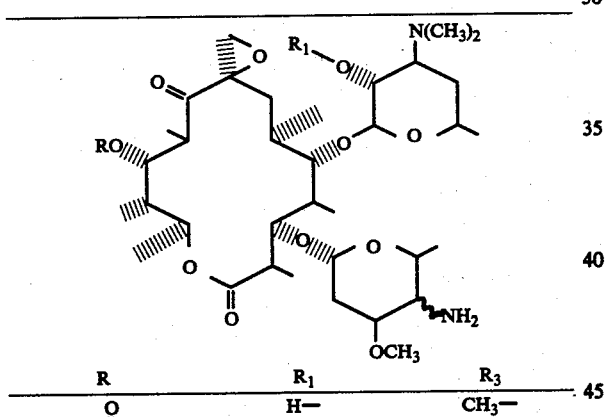

| R | $R_1$ | $R_3$ |
|---|---|---|
| $CH_3\overset{O}{\underset{\|}{C}}-$ | H— | $CH_3-$ |
| $CH_3\overset{O}{\underset{\|}{C}}-$ | H— | $n\text{-}C_3H_7-$ |
| $CH_3\overset{O}{\underset{\|}{C}}-$ | H— | $i\text{-}C_3H_7-$ |
| $CH_3\overset{O}{\underset{\|}{C}}-$ | H— | $n\text{-}C_5H_{11}-$ |
| $CH_3\overset{O}{\underset{\|}{C}}-$ | $CH_3\overset{O}{\underset{\|}{C}}-$ | $C_2H_5-$ |
| $CH_3\overset{O}{\underset{\|}{C}}-$ | $CH_3\overset{O}{\underset{\|}{C}}-$ | $i\text{-}C_3H_7-$ |
| $CH_3\overset{O}{\underset{\|}{C}}-$ | $CH_3\overset{O}{\underset{\|}{C}}-$ | $t\text{-}C_4H_9-$ |
| $CH_3\overset{O}{\underset{\|}{C}}-$ | $CH_3CH_2\overset{O}{\underset{\|}{C}}-$ | $CH_3-$ |
| $CH_3\overset{O}{\underset{\|}{C}}-$ | $CH_3CH_2\overset{O}{\underset{\|}{C}}-$ | $n\text{-}C_6H_{13}-$ |
| $CH_3\overset{O}{\underset{\|}{C}}-$ | $CH_3CH_2\overset{O}{\underset{\|}{C}}-$ | $i\text{-}C_5H_{11}-$ |

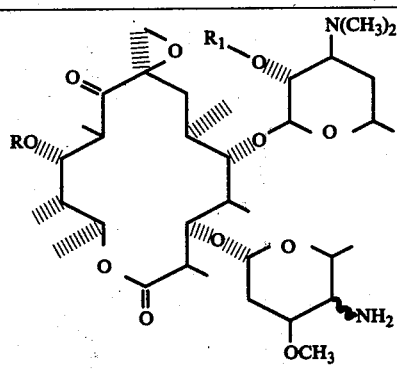

| R | $R_1$ | $R_3$ |
|---|---|---|
| $CH_3CH_2\overset{O}{\underset{\|}{C}}-$ | H— | $n\text{-}C_3H_7-$ |
| $CH_3CH_2\overset{O}{\underset{\|}{C}}-$ | H— | $n\text{-}C_4H_9-$ |
| $CH_3CH_2\overset{O}{\underset{\|}{C}}-$ | H— | $n\text{-}C_6H_{13}-$ |
| $CH_3CH_2\overset{O}{\underset{\|}{C}}-$ | $CH_3\overset{O}{\underset{\|}{C}}-$ | $CH_3-$ |
| $CH_3CH_2\overset{O}{\underset{\|}{C}}-$ | $CH_3\overset{O}{\underset{\|}{C}}-$ | $i\text{-}C_3H_7-$ |
| $CH_3CH_2\overset{O}{\underset{\|}{C}}-$ | $CH_3\overset{O}{\underset{\|}{C}}-$ | $n\text{-}C_5H_{11}-$ |
| $CH_3CH_2\overset{O}{\underset{\|}{C}}-$ | $CH_3\overset{O}{\underset{\|}{C}}-$ | $i\text{-}C_5H_{11}-$ |
| $CH_3CH_2\overset{O}{\underset{\|}{C}}-$ | $CH_3CH_2\overset{O}{\underset{\|}{C}}-$ | $C_2H_5-$ |
| $CH_3CH_2\overset{O}{\underset{\|}{C}}-$ | $CH_3CH_2\overset{O}{\underset{\|}{C}}-$ | $n\text{-}C_6H_{13}-$ |
| $CH_3CH_2\overset{O}{\underset{\|}{C}}-$ | $CH_3CH_2\overset{O}{\underset{\|}{C}}-$ | $i\text{-}C_4H_9-$ |
| H— | H— | $CH_3-$ |
| H— | H— | $C_2H_5-$ |
| H— | H— | $t\text{-}C_4H_9-$ |
| H— | H— | $i\text{-}C_5H_{11}-$ |
| H— | H— | $n\text{-}C_6H_{13}-$ |

EXAMPLE 58

11-Acetyl-4''-deoxy-4''-dimethylamino-oleandomycin

Two grams of 11-acetyl-4''-deoxy-4''-amino-oleandomycin, 1 g. of 10% palladium-on-charcoal and 2.06 ml. of formalin solution are combined in 40 ml. of methanol and shaken in a hydrogen atmosphere at an initial pressure of 50 p.s.i. overnight. The spent catalyst is filtered and the filtrate concentrated to dryness under reduced pressure. The residual product (1.97 g.) is chromatographed on 40 g. of silica gel using chloroform as the initial eluate. After fraction #25, which comprised 650 drops per fraction, the eluate is changed to 3% methanol in chloroform. Fractions 36–150 are combined and concentrated in vacuo to give 704 mg. of the desired product as a white foam.

NMR ($\delta$, $CDCl_3$): 3.33 (3H)s, 2.63 (2H)m, 2.30 (12H)s and 2.10 (3H)s.

EXAMPLE 59

Employing the procedure of Example 58, with the exception that isopropanol is used as the solvent, and starting with the requisite 4"-deoxy-4"-amino-oleandomycin, the following compounds are synthesized:

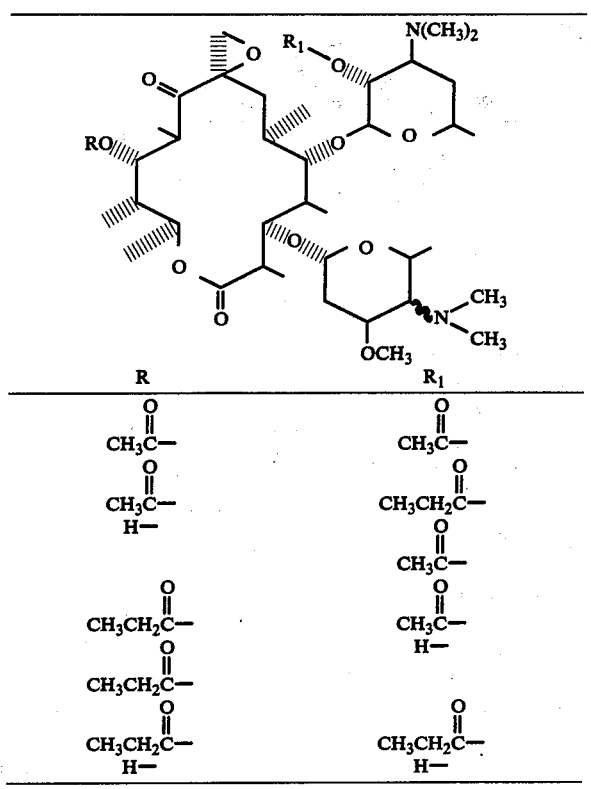

| R | R₁ |
|---|---|
| CH₃C(O)— | CH₃C(O)— |
| CH₃C(O)— | O |
| H— | CH₃CH₂C(O)— |
| | CH₃C(O)— |
| CH₃CH₂C(O)— | CH₃C(O)— |
| CH₃CH₂C(O)— | H— |
| CH₃CH₂C(O)— | |
| H— | CH₃CH₂C(O)— |
| | H— |

EXAMPLE 60

11-Acetyl-4"-deoxy-4"-amino-oleandomycin dihydrochloride

To 7.28 g. of 11-acetyl-4"-deoxy-4"-amino-oleandomycin in 50 ml. of dry ethyl acetate is added 20 ml. of a 1N ethyl acetate solution of hydrogen chloride, and the resulting solution concentrated to dryness under reduced pressure. The residual material is triturated with ether and filtered to give the desired salt.

By a similar procedure the amine compounds of the present invention are converted to their di-acid addition salts.

EXAMPLE 61

11,2'-Diacetyl-4"-deoxy-4"-amino-oleanodomycin hydrochloride

The procedure of Example 60 is repeated with the exception that 10 ml. of a 1N ethyl acetate solution of hydrogen chloride is added. The solution is concentrated to dryness in vacuo and the residual mono-hydrochloride salt is triturated with ether and filtered.

By a similar procedure the amine compounds of the present invention are converted to their mono-acid addition salts.

EXAMPLE 62

11-Acetyl-4"-deoxy-4"-amino-oleandomycin aspartate

To 960 mg. of 11-acetyl-4"-deoxy-4"-amino-oleandomycin in 6 ml. of acetone at 40° C. is added 18 ml. of water followed by 175 mg. of aspartic acid. The mixture is heated to reflux until a hazy solution is affected. The mixture is filtered hot and the clear filtrate is concentrated to remove the acetone. The remaining solution is then freeze-dried to give the product as the residual material.

PREPARATION A

2'-Acetyl-8,8a-deoxy-8,8a-dihydro-oleandomycin 1a. 2'-Acetyl-8,8a-deoxy-oleandomycin A 250 ml., 3-necked round bottom flask is charged with zinc dust (10 g.) and mercuric chloride (1 g.). After the solids are mixed well, 1N HCl (25 ml.) is added and the mixture is stirred vigorously for 15 min. The aqueous supernate is removed and fresh 1N HCl (25 ml.) added and the flask placed under a carbon dioxide atmosphere. A filtered solution of chromium trichloride (50 g. in 65 ml. of 1N HCl) is added rapidly to the zinc amalgam. The mixture is stirred under a carbon dioxide atmosphere for 1 hr. during which time a light blue color develops indicating the presence of chromous chloride (CrCl₂). Stirring is discontinued after 1 hr. and the zinc amalgam allowed to settle to the bottom of the flask.

A solution of 2'-acetyl-oleandomycin (29.2 g.) in acetone (200 ml.) and water (100 ml.) is placed in a dropping funnel attached to a 600 ml., 3-necked round bottom flask equipped with an overhead mechanical stirrer. To this flask is added, under a carbon dioxide atmosphere and with stirring, the solution of 2'-acetyl-oleandomycin and the previously prepared solution of chromous chloride. The solutions are added simultaneously at such a rate that both finished at the same time. The addition takes about 12 min. After 35 min. of stirring at room temperature, water (100 ml.) and ethyl acetate (100 ml.) are added to the reaction and stirring continued for 15 min. The ethyl acetate layer is separated and washed with water (80 ml.). The ethyl acetate is separated and the aqueous extracts combined and washed with fresh ethyl acetate (100 ml.). The ethyl acetate layer is separated and washed with water (100 ml.). The organic phase is separated and the aqueous washes combined and treated with sodium chloride (75 g.). The additional ethyl acetate which separates is syphoned off and combined with the other ethyl acetate extracts. Water is added to the combined ethyl acetate extracts and adjusted to pH 8.5 with sodium bicarbonate. The organic layer is separated, washed with water, saturated sodium chloride and dried over anhydrous sodium sulfate. Filtration and evaporation of the solvents under reduced pressure affords a white solid which is crystalized from ethyl acetate/heptane to give the desired compound, 8.4 g., m.p. 183.5°–185° C.

Anal. Calc'd. for $C_{37}H_{63}O_{13}N$: C, 62.2; H, 9.0; N, 2.0. Found: C, 62.0; H, 8.9; N, 2.0.

NMR (δ, CDCl₃): 5.63 (1H)s, 5.58 (1H)s, 3.43 (3H)s, 2.36 (6H)s and 2.08 (3H)s.

1b. 2'-Acetyl-8,8a-deoxy-8,8a-dihydro-oleandomycin

Aluminum foil (4.0 g.) cut into ¼ inch pieces and covered with 290 ml. of an aqueous mercuric chloride solution is stirred for 30–45 sec. The solution is decanted and the amalgamated aluminum washed successively with water (2×), isopropanol (1×) and tetrahydrofuran (1×). The pieces are layered over with 45 ml. of tetrahydrofuran, 45 ml. of isopropanol and 10 ml. of water and subsequently cooled to 0° C. in an ice bath. A solution of 2.0 g. of 8,8a-deoxy-2'-acetyl-oleandomycin in tetrahydrofuran, isopropanol and water is added dropwise to the amalgamated aluminum at such a rate that the temperature remains at 0° C. When the addition is complete the bath is removed and the reaction mixture allowed to stir at room temperature overnight. The solids are filtered and the filtrate concentrated in vacuo to dryness. The residue is treated with ethyl acetate - water and the pH adjusted to 9.0 with a saturated sodium carbonate solution. The organic phase is separated, washed with water and a saturated brine solution and dried over sodium sulfate. Removal of the solvent gives 2.27 g. of the desired product.

PREPARATION B 2a.
11,2'-Diacetyl-8,8a-deoxy-8,8a-methylene-oleandomycin

In a flame dried 200 ml. three-necked flask equipped with a dropping funnel, magnetic stirrer and a positive-pressure nitrogen inlet is combined 16.4 g. of trimethysulfoxonium iodide and 3.4 g. of a 50% oil dispersion of sodium hydride. The solids are mixed well and 43.2 ml. of dimethylsulfoxide is added via the dropping funnel. After 1 hour, when the evolution of hydrogen has stopped, the suspension is cooled to 5°-10° C. and a solution of 22.6 g. of 11,2'-diacetyl-8,8a-deoxy-oleandomycin in 32 ml. of tetrahydrofuran and 16 ml. of diemthylsulfoxide is added over a 10 min. period. The suspension is stirred at room temperature for 90 min. and poured in 300 ml. of water and extracted with two 300 ml. portions of ethyl acetate. The organic extracts are washed with water, saturated solution of sodium chloride, dried over anhydrous sodium sulfate, filtered, and evaporated to dryness under reduced pressure. The residue is crystallized from ether to give 8.9 g. of 11,2'-diacetyl-8,8a-deoxy-8,8a-methylene-oleandomycin.

What is claimed is:

1. A compound selected from the group consisting of:

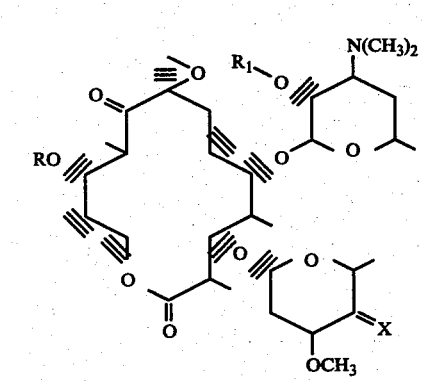

I

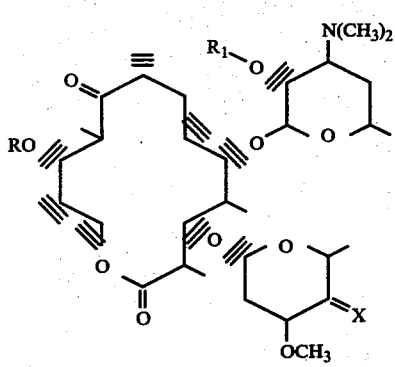

II and

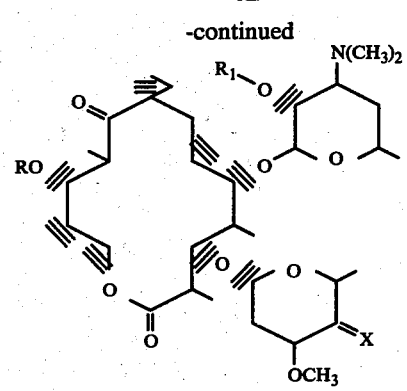

III wherein R and $R_1$ are each selected from the group consisting of hydrogen and alkanoyl having two to three carbon atoms; and X is selected from the group consisting of O, N—OH, N—OCH$_3$ and $$N-O-\overset{O}{\underset{\|}{C}}CH_3.$$

2. A compound of claim 1 of Formula I.
3. A compound of claim 2 wherein X is O.
4. The compound of claim 3 wherein R and $R_1$ are each acetyl.
5. The compound of claim 3 wherein R is acetyl and $R_1$ is hydrogen.
6. The compound of claim 3 wherein R and $R_1$ are each hydrogen.
7. The compound of claim 3 wherein R is hydrogen and $R_1$ is acetyl.
8. A 4''-amino epimeric compound selected from the group consisting of:

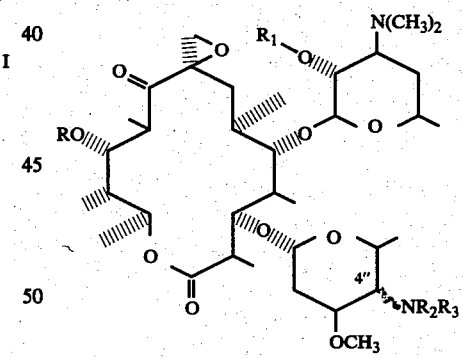

IV

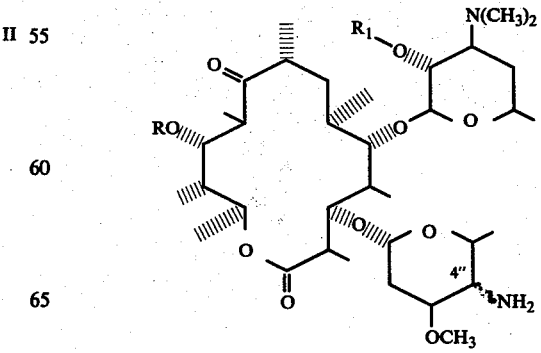

V

-continued

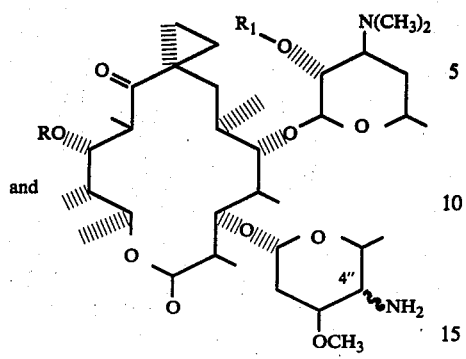

VI and the pharmaceutically acceptable acid addition salts thereof, wherein R and $R_1$ are each selected from the group consisting of hydrogen and alkanoyl having two to three carbon atoms; $R_2$ is selected from the group consisting of hydrogen and methyl; and $R_3$ is selected from the group consisting of hydrogen and alkyl having from one to six carbon atoms provided that when $R_2$ is methyl, $R_3$ is methyl.

9. A compound of the formula:

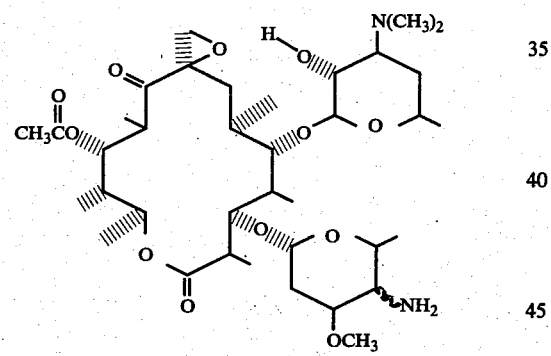

10. A compound of the formula:

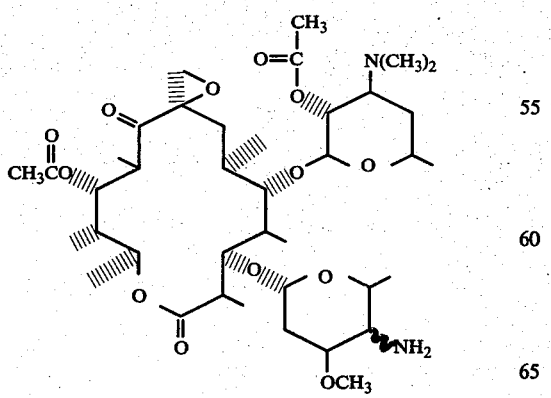

11. A compound of the formula

12. A compound of the formula:

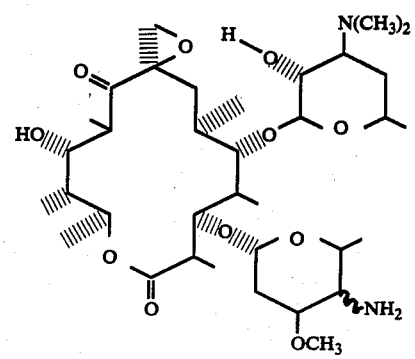

13. A compound of the formula:

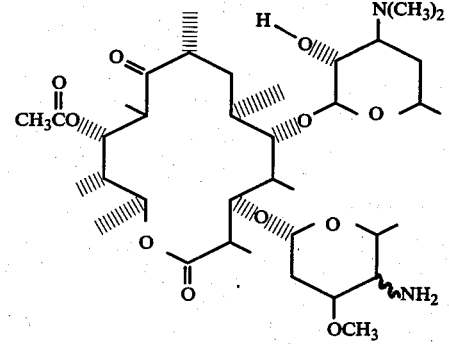

14. A compound of the formula:

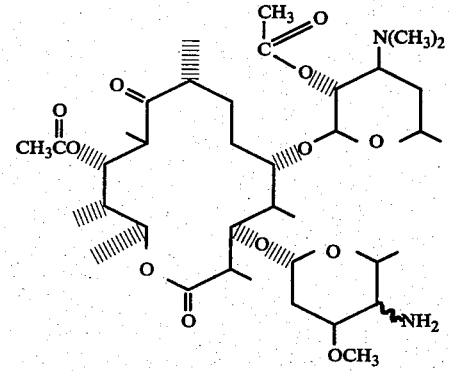

15. A compound of the formula:

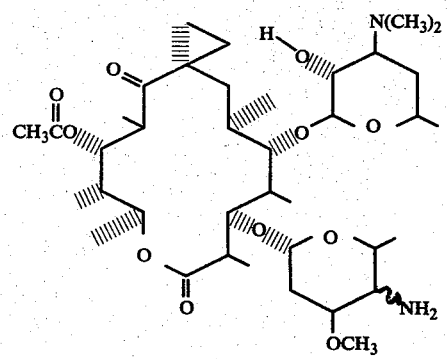

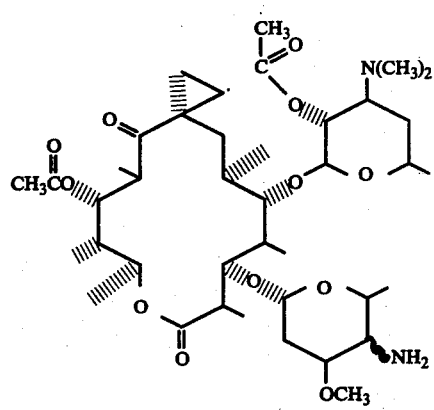

16. A process for preparing a compound selected from the group consisting of:

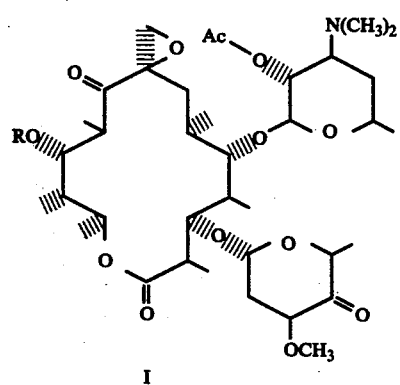

I

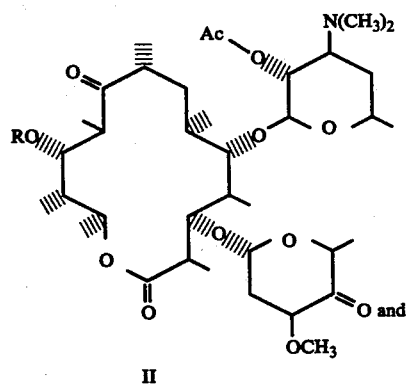

II

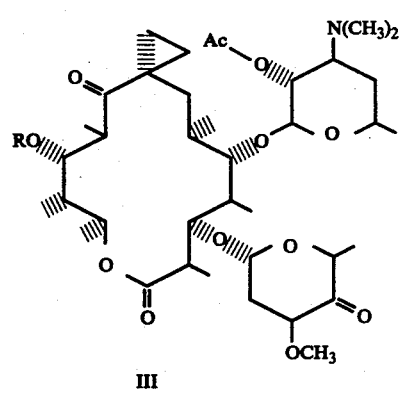

III wherein R is selected from the group consisting of hydrogen and alkanoyl having two to three carbon atoms and Ac is alkanoyl having two, to three carbon atoms which comprises reacting, respectively, a compound selected from the group consisting of:

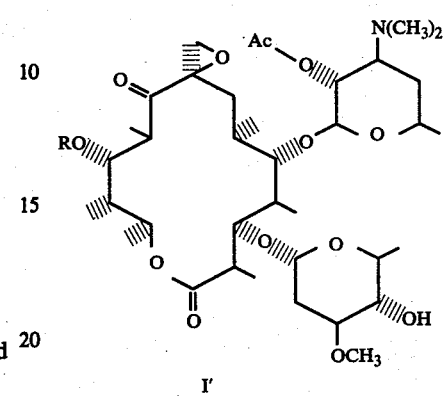

I'

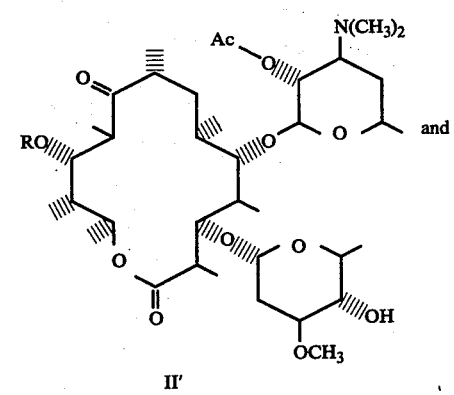

II'

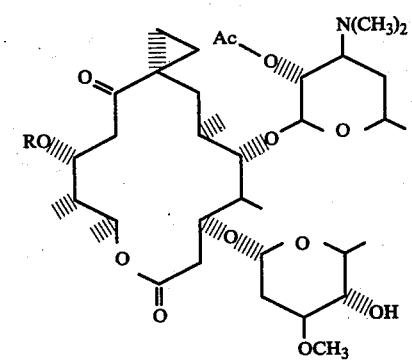

III' with one mole each of N-chlorosuccinimide and dimethylsulfide in a reaction-inert solvent at about 0° to −25° C. followed by contacting the reaction mixture with one mole of triethylamine.

17. The process of claim 16 wherein the reaction-inert solvent is toluene-benzene.

18. The process of claim 17 for preparing the compound of Formula I.

19. The process of claim 18 wherein R and Ac are each acetyl.

20. The process of claim 18 wherein R is hydrogen and Ac is acetyl.

* * * * *